(12) United States Patent
Fathallah-Shaykh et al.

(10) Patent No.: US 12,198,334 B2
(45) Date of Patent: Jan. 14, 2025

(54) METHOD FOR DETECTING RADIOLOGICAL PROGRESSION IN CANCER SURVEILLANCE

(71) Applicants: THE UAB RESEARCH FOUNDATION, Birmingham, AL (US); Rowan University, Glassboro, NJ (US)

(72) Inventors: Hassan Fathallah-Shaykh, Birmingham, AL (US); Nidhal Bouaynaya, Voorhees, NJ (US)

(73) Assignees: The UAB Research Foundation, Birmingham, AL (US); Rowan University, Glassboro, NJ (US)

( * ) Notice: Subject to any disclaimer, the term of this patent is extended or adjusted under 35 U.S.C. 154(b) by 367 days.

(21) Appl. No.: 17/600,703

(22) PCT Filed: Apr. 1, 2020

(86) PCT No.: PCT/US2020/026113
§ 371 (c)(1),
(2) Date: Oct. 1, 2021

(87) PCT Pub. No.: WO2020/205931
PCT Pub. Date: Oct. 8, 2020

(65) Prior Publication Data
US 2022/0172359 A1 Jun. 2, 2022

Related U.S. Application Data

(60) Provisional application No. 62/828,871, filed on Apr. 3, 2019, provisional application No. 62/828,239, filed on Apr. 2, 2019.

(51) Int. Cl.
G06T 7/00 (2017.01)
A61B 5/00 (2006.01)
(Continued)

(52) U.S. Cl.
CPC .......... *G06T 7/0012* (2013.01); *A61B 5/4842* (2013.01); *G06T 7/62* (2017.01);
(Continued)

(58) Field of Classification Search
CPC .................... G06T 7/0012; G06T 7/62; G06T 2207/10088; G06T 2207/10104; G06T 2207/30096; G16H 50/30; A61B 5/4842
See application file for complete search history.

(56) References Cited

U.S. PATENT DOCUMENTS

2007/0027408 A1 2/2007 Fitzgerald et al.
2015/0165225 A1* 6/2015 Nadobny ............... A61N 2/004
607/103

(Continued)

OTHER PUBLICATIONS

International Search Report and Written Opinion for PCT/US2020/0205931 mailed on Jun. 17, 2020.
(Continued)

*Primary Examiner* — John J Lee
(74) *Attorney, Agent, or Firm* — Thomas|Horstemeyer, LLP

(57) ABSTRACT

A method and computer-based system is provided that assists physicians in detecting early tumor growth and allowing modification of treatment to have a positive impact on medical management, patient morbidity, outcomes and survival times. The method comprises measuring tumor volumes from radiological images to predict growth by a statistical method. The methods allow detection of increases in tumor size earlier than is currently possible and, therefore, advantageous in modifying or optimizing treatment.

6 Claims, 14 Drawing Sheets

(51) Int. Cl.
  *G06T 7/62* (2017.01)
  *G16H 50/30* (2018.01)
(52) U.S. Cl.
  CPC .............. *G16H 50/30* (2018.01); *G06T 2207/10088* (2013.01); *G06T 2207/10104* (2013.01); *G06T 2207/30096* (2013.01)

(56) References Cited

U.S. PATENT DOCUMENTS

| | | | |
|---|---|---|---|
| 2016/0296126 A1* | 10/2016 | Berry | A61B 5/489 |
| 2017/0238867 A1* | 8/2017 | Javed | A61B 5/746 |
| 2018/0042567 A1* | 2/2018 | Smith | A61B 6/5211 |

OTHER PUBLICATIONS

Rasmussen BK, et al., "Epidemiology of glioma: clinical characteristics, symptoms, and predictors of glioma patients grade I-IV in the the Danish Neuro-Oncology Registry",. J Neurooncol. 2017;135(3):571-9. Epub Sep. 2, 2017. doi: 10.1007/s11060-017-2607-5. PubMed PMID: 28861666.

Berntsson S G., et al. "Glioma-related seizures in relation to histopathological subtypes: a report from the glioma International case-control study". J Neurol. 2018;265(6):1432-42. Epub Apr. 25, 2018. doi: 10.1007/s00415-018-8857-0. PubMed PMID: 29687214; PubMed Central PMCID: PMCPMC5990563.

Bynevelt M et al., "FLAIR imaging in the follow-up of low-grade gliomas: time to dispense with the dual-echo"? Neuroradiology. 2001;43(2):129-33. Epub May 1, 2001. PubMed PMID: 11326557.

Delgado-Lopez PD, "Diffuse low-grade glioma: a review on the new molecular classification, natural history and current management strategies"., Clin Transl Oncol. 2017;19(8):931-44. Epub Mar. 4, 2017. doi: 10.1007/s12094-017-1631-4. PubMed PMID: 28255650.

Buckner J., et al., "Management of diffuse low-grade gliomas in adults—use of molecular diagnostics"., Nat Rev Neurol. 2017;13(6):340-51. Epub May 13, 2017. doi: 10.1038/nmeurol.2017.54. PubMed PMID: 28497806.

Le Rhun E., "Current Management of Adult Diffuse Infiltrative Low Grade Gliomas"., Curr Neurol Neurosci Rep. 2016;16(2):15. Epub Jan. 12, 2016. doi: 10.1007/s11910-015-0615-4. PubMed PMID: 26750130.

Claus EB., et al., "Survival rates in patients with low-grade glioma after intraoperative magnetic resonance image guidance"., Cancer. 2005;103(6):1227-33. Epub Feb. 4, 2005. doi: 10.1002/cncr.20867. PubMed PMID: 15690327.

Johannesen TB. et al., "Progress in long-term survival in adult patients with supratentorial low-grade gliomas: a population-based study of 993 patients in whom tumors were diagnosed between 1970 and 1993"., J Neurosurg. 2003;99(5):854-62. Epub Nov. 12, 2003. doi: 10.3171/jns.2003.99.5.0854. PubMed PMID: 14609165.

McGirt MJ., et al., "Independent association of extent of resection with survival in patients with malignant brain astrocytoma", J Neurosurg. 2009;110(1):156-62. Epub Oct. 14, 2008. doi: 10.3171/2008.4.17536. PubMed PMID: 18847342.

Nakamura M., et al., "Analysis of prognostic and survival factors related to treatment of low-grade astrocytomas in adults"., Oncology. 2000;58(2):108-16. Epub Mar. 8, 2000. doi: 10.1159/000012087. PubMed PMID: 10705237.

Ahmadi R, et al., "Long-term outcome and survival of surgically treated supratentorial low-grade glioma in adult patients"., Acta Neurochir (Wien). 2009;151(11):1359-65. Epub Jul. 4, 2009/. doi: 10.1007/s00701-009-0435-x. PubMed PMID: 19575144.

Smith JS., et al., "Role of extent of resection in the long-term outcome of low-grade hemispheric gliomas"., J Clin Oncol. 2008;26(8):1338-45. Epub Mar. 8, 2008. doi: 10.1200/JCO.2007.13.9337. PubMed PMID: 18323558.

Sanai N., "Glioma extent of resection and its impact on patient outcome"., Neurosurgery. 2008;62(4):753-64; discussion 264-6. Epub May 23, 2008. doi: 10.1227/01.neu.0000318159.21731.cf. PubMed PMID: 18496181.

Surma-aho O., "Adverse long-term effects of brain radiotherapy in adult low-grade glioma patients". Neurology. 2001;56(10):1285-90. Epub May 29, 2001. PubMed PMID: 11376174.

Lena Ek, et al., "Decline in executive functions and speed in suspected low-grade gliomas: A 3-year follow-up of a clinical cohort"., Appl Neuropsychol Adult. 2018;25(4):376-84. Epub May 4, 2017. doi: 10.1080/23279095.2017.1316506. PubMed PMID: 28467112.

Reijneveld Jaap C., et al., Health-related quality of life in patients with high-risk low-grade glioma (EORTC 22033-26033): a randomised, open-label, phase 3 intergroup study., Lancet Oncol. 2016; 17(11):1533-42. Epub Oct. 1, 2016. doi: 10.1016/S1470-2045(16)30305-9. PubMed PMID: 27686943.

Scribner E., et al., "Key rates for the grades and transformation ability of glioma: model simulations and clinical cases"., J Neurooncol. 2017;133(2):377-88. Epub Apr. 30, 2017. doi: 10.1007/s11060-017-2444-6. PubMed PMID: 28451993.

Baumert B. G., et al., "Temozolomide chemotherapy versus radiotherapy in high-risk low-grade glioma (EORTC 22033-26033): a randomised, open-label, phase 3 intergroup study"., Lancet Oncol. 2016;17(11):1521-32. Epub Oct. 1, 2016. doi: 10.1016/S1470-2045(16)30313-8. PubMed PMID: 27686946; PubMed Central PMCID: PMCPMC5124485.

Jhaveri J., et al., "Is less more? Comparing chemotherapy alone with chemotherapy and radiation for high-risk grade 2 glioma: An analysis of the National Cancer Data Base"., Cancer. 2018;124(6):1169-78. Epub Dec. 6, 2017. doi: 10.1002/cncr.31158. PubMed PMID: 29205287.

Wang S. et al., "Pathological Brain Detection by Artificial Intelligence in Magnetic Resonance Imaging Scanning",. Progress In Electromagnetics Research., 2016;156:105-33. doi: 10.2528/PIER16070801.

Dera D. et al., "Automated Robust Image Segmentation: Level Set Method Using Nonnegative Matrix Factorization with Application to Brain MRI"., Bull Math Biol. 2016;78(7):1450-76. Epub Jul. 16, 2016. doi: 10.1007/s11538-016-0190-0. PubMed PMID: 27417984.

Darkhovski Boris S., "Nonparametric Methods in Change-Point Problems: A General Approach and Some Concrete Algorithms", Lecture Notes-Monograph Series , 1994, vol. 23, Change-Point Problems (1994), pp. 99-107, Institute of Mathematical Statistics, https://www.jstor.org/stable/4355766.

Killick R FP, Eckley I., "Optimal detection of changepoints with a linear computational cost". Journal of the American Statistical Association., 2012;107(500):1590-8.

Kerkhof M. et al., "Interobserver variability in the radiological assessment of magnetic resonance imaging (MRI) Including perfusion MRI in glioblastoma multiforme"., Eur J Neurol. 2016;23(10):1528-33. Epub Jul. 19, 2016. doi: 10.1111/ene.13070. PubMed PMID: 27424939.

Bakas S, et al., Identifying the Best Machine Learning Algorithms for Brain Tumor Segmentation, Progression Assessment, and Overall Survival Prediction in the BRATS Challenge. arXiv:181102629. 2018.

Scribner E., "Effects of anti-angiogenesis on glioblastoma growth and migration: model to clinical predictions". PLoS One. 2014;9(12):e115018. Epub Dec. 17, 2014. doi: 10.1371/journal.pone.0115018. PubMed PMID: 25506702; PubMed Central PMCID: PMCPMC4266618.

Raman F., et al., "Computational Trials: Unraveling Motility Phenotypes, Progression Patterns, and Treatment Options for Glioblastoma Multiforme"., PLoS One. 2016;11(1):e0146617. Epub Jan. 13, 2016/01/13. doi: 10.1371/journal.pone.0146617. PubMed PMID: 26756205; PubMed Central PMCID: PMCPMC4710507.

* cited by examiner

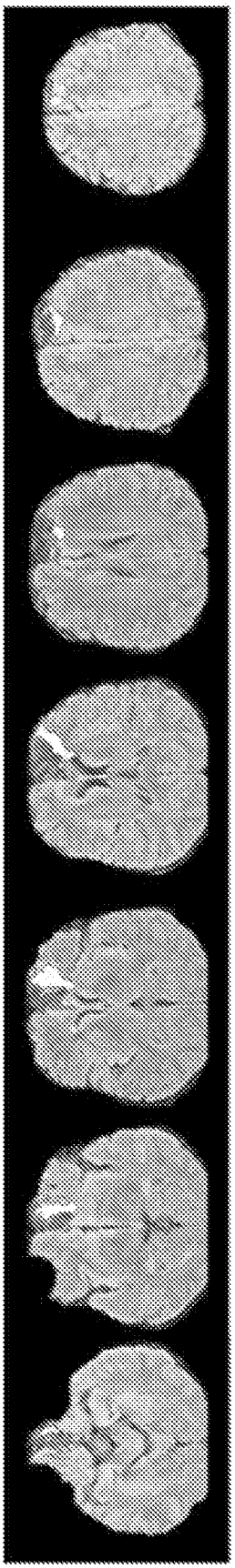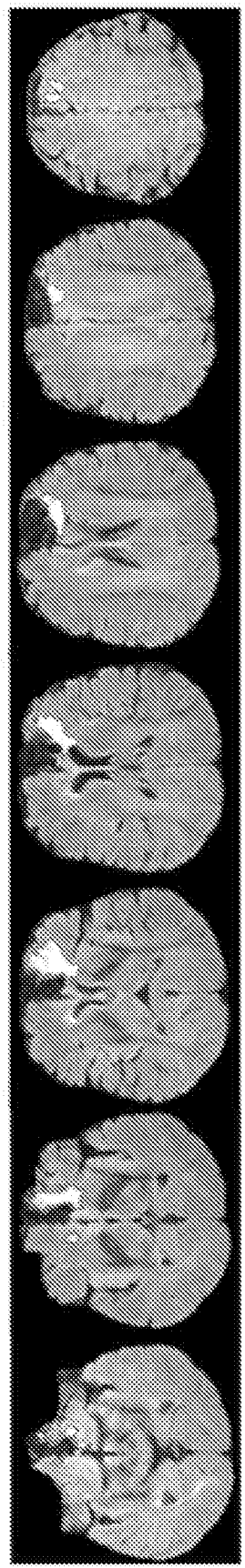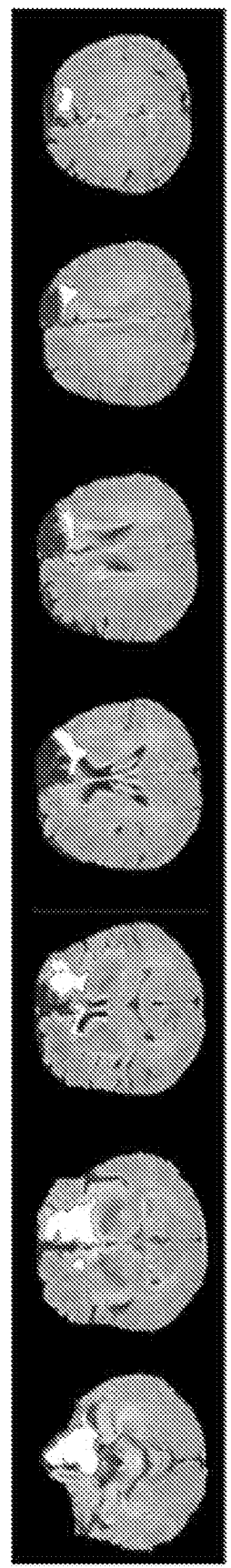

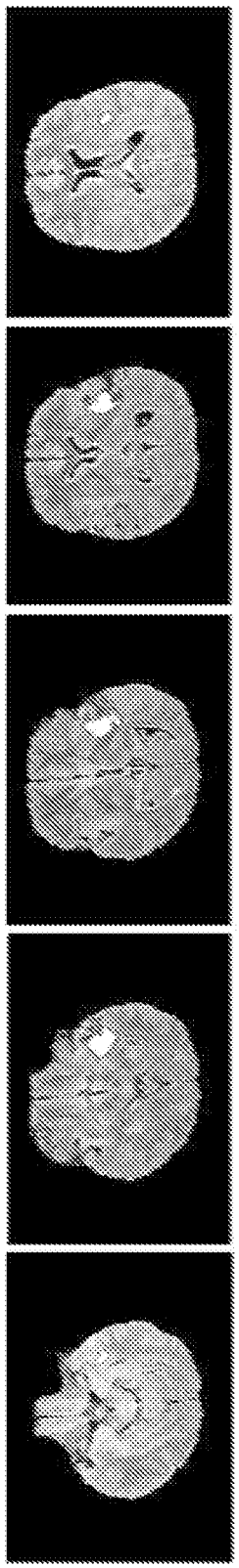
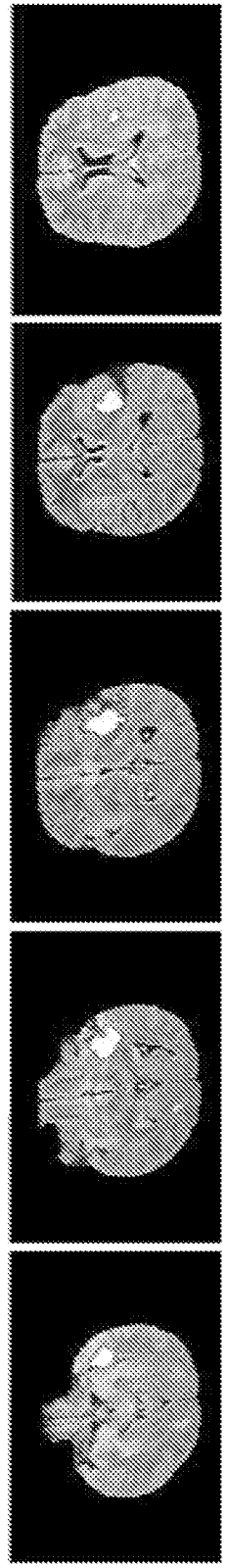
Fig. 3A  Fig. 3B  Fig. 3C  Fig. 3D  Fig. 3E
Fig. 3F  Fig. 3G  Fig. 3H  Fig. 3I  Fig. 3J

| Case Number | Pathology/Imaging | Interval to Time 1 | CAD Dx Time 1 | VC Dx Time 1 | Interval to Last MRI | CAD Dx Last MRI | VC Dx LAST MRI | GROL |
|---|---|---|---|---|---|---|---|---|
| 4224 | oligodendroglioma | 21 months | GROWTH | STABLE | 108 months | GROWTH | GROWTH | 1 |
| 4225 | oligodendroglioma | 8 months | GROWTH | STABLE | 80 months | GROWTH | GROWTH | 1 |
| 6934 | oligodendroglioma | 18 months | GROWTH | STABLE | 79 months | GROWTH | GROWTH | 1 |
| 7489 | oligodendroglioma | 11 months | GROWTH | STABLE | 51 months | GROWTH | GROWTH | 1 |
| 7490 | oligodendroglioma | 23 months | GROWTH | STABLE | 154 months | GROWTH | GROWTH | 1 |
| 7491 | oligodendroglioma | 30 months | GROWTH | STABLE | 46 months | GROWTH | GROWTH | 1 |
| 7492 | oligodendroglioma | 9 months | GROWTH | STABLE | 16 months | GROWTH | STABLE | 2 |
| 7493 | oligodendroglioma | 10 months | GROWTH | STABLE | 22 months | GROWTH | STABLE | 2 |
| 7494 | oligodendroglioma | 13 months | GROWTH | STABLE | 37 months | GROWTH | STABLE | 2 |
| 7504 | oligodendroglioma | 20 months | GROWTH | STABLE | 90 months | GROWTH | STABLE | 2 |
| 7505 | oligodendroglioma | 19 months | GROWTH | STABLE | 31 months | GROWTH | GROWTH | 1 |
| 7506 | oligodendroglioma | | | | 19 months | STABLE | STABLE | 2 |
| 7729 | oligodendroglioma | | | | 8 months | STABLE | STABLE | 2 |
| 7730 | oligodendroglioma | | | | 47 months | STABLE | STABLE | 2 |
| 7733 | oligodendroglioma | 15 months | GROWTH | STABLE | 89 months | GROWTH | STABLE | 2 |
| 7734 | oligodendroglioma | | | | 19 months | STABLE | STABLE | 2 |
| 7735 | oligodendroglioma | | | | 19 months | STABLE | STABLE | 2 |
| 7736 | oligodendroglioma | 25 months | GROWTH | STABLE | 88 months | GROWTH | STABLE | 2 |
| 7741 | oligodendroglioma | 45 months | GROWTH | STABLE | 81 months | GROWTH | STABLE | 2 |
| 4386 | astrocytoma | 11 months | GROWTH | STABLE | 32 months | GROWTH | GROWTH | 1 |
| 4388 | astrocytoma | 11 months | GROWTH | STABLE | 14 months | GROWTH | GROWTH | 1 |
| 4389 | astrocytoma | 14 months | GROWTH | STABLE | 26 months | GROWTH | GROWTH | 1 |
| 6937 | astrocytoma | 16 months | GROWTH | STABLE | 47 months | GROWTH | GROWTH | 1 |
| 6938 | astrocytoma | 10 months | GROWTH | STABLE | 13 months | GROWTH | GROWTH | 1 |
| 7069 | astrocytoma | | | | 25 months | GROWTH | GROWTH | 1 |
| 7070 | astrocytoma | 13 months | GROWTH | STABLE | 108 months | GROWTH | GROWTH | 1 |
| 7094 | astrocytoma | 11 months | GROWTH | STABLE | 51 months | GROWTH | GROWTH | 1 |
| 7333 | astrocytoma | 19 months | GROWTH | STABLE | 44 months | GROWTH | GROWTH | 1 |
| 7336 | astrocytoma | 19 months | GROWTH | STABLE | 34 months | GROWTH | GROWTH | 1 |
| 7469 | astrocytoma | 20 months | GROWTH | STABLE | 40 months | GROWTH | GROWTH | 1 |

*Fig. 8*

| Case Number | Pathology/Imaging | Interval to Time 1 | CAD Dx Time 1 | VC Dx Time 1 | Interval to Last MRI | CAD Dx Last MRI | VC Dx LAST MRI | GROL |
|---|---|---|---|---|---|---|---|---|
| 7470 | astrocytoma | 10 months | GROWTH | STABLE | 21 months | GROWTH | GROWTH | 1 |
| 7472 | astrocytoma | 10 months | GROWTH | STABLE | 22 months | GROWTH | STABLE | 2 |
| 7474 | astrocytoma | 9 months | GROWTH | STABLE | 32 months | GROWTH | GROWTH | 1 |
| 7477 | astrocytoma | 7 months | GROWTH | STABLE | 26 months | GROWTH | GROWTH | 1 |
| 7707 | astrocytoma | | | | 10 months | GROWTH | GROWTH | 1 |
| 7708 | astrocytoma | 8 months | GROWTH | STABLE | 25 months | GROWTH | STABLE | 2 |
| 7709 | astrocytoma | 14 months | GROWTH | STABLE | 38 months | GROWTH | GROWTH | 1 |
| 7710 | astrocytoma | | | | 4 months | STABLE | STABLE | 2 |
| 7711 | astrocytoma | | | | 9 months | GROWTH | GROWTH | 1 |
| 7713 | astrocytoma | 8 months | GROWTH | STABLE | 21 months | GROWTH | STABLE | 2 |
| 7714 | astrocytoma | | | | 69 months | STABLE | STABLE | 2 |
| 7715 | astrocytoma | | | | 7 months | STABLE | STABLE | 2 |
| 7716 | astrocytoma | | | | 15 months | GROWTH | STABLE | 2 |
| 7727 | astrocytoma | | | | 9 months | GROWTH | GROWTH | 1 |
| 7732 | astrocytoma | | | | 29 months | STABLE | STABLE | 2 |
| 4384 | mixed glioma | 20 months | GROWTH | STABLE | 47 months | GROWTH | GROWTH | 1 |
| 4385 | mixed glioma | 9 months | GROWTH | STABLE | 24 months | GROWTH | GROWTH | 1 |
| 4387 | mixed glioma | 11 months | GROWTH | STABLE | 73 months | GROWTH | GROWTH | 1 |
| 6935 | mixed glioma | 31 months | GROWTH | STABLE | 112 months | GROWTH | GROWTH | 1 |
| 7334 | mixed glioma | | | | 11 months | GROWTH | GROWTH | 1 |
| 7335 | mixed glioma | 12 months | GROWTH | STABLE | 34 months | GROWTH | GROWTH | 1 |
| 7371 | mixed glioma | 9 months | GROWTH | STABLE | 101 months | GROWTH | STABLE | 2 |
| 7476 | mixed glioma | 21 months | GROWTH | STABLE | 28 months | GROWTH | GROWTH | 1 |
| 7478 | mixed glioma | 20 months | GROWTH | STABLE | 65 months | GROWTH | GROWTH | 1 |
| 7717 | mixed glioma | 9 months | GROWTH | STABLE | 66 months | GROWTH | GROWTH | 1 |
| 7728 | mixed glioma | 7 months | GROWTH | STABLE | 73 months | GROWTH | GROWTH | 1 |
| 7749 | Imaging Abnormality | | | | 33 months | STABLE | STABLE | 2 |
| 7751 | Imaging Abnormality | | | | 110 months | STABLE | STABLE | 3 |
| 7752 | Imaging Abnormality | | | | 25 months | STABLE | STABLE | 3 |
| 7753 | Imaging Abnormality | | | | 99 months | STABLE | STABLE | 3 |
| 7754 | Imaging Abnormality | | | | 79 months | STABLE | STABLE | 3 |
| 7755 | Imaging Abnormality | | | | 86 months | STABLE | STABLE | 3 |
| 7756 | Imaging Abnormality | | | | 13 months | STABLE | STABLE | 3 |

*Fig. 8-cont'd*

METHOD FOR DETECTING RADIOLOGICAL PROGRESSION IN CANCER SURVEILLANCE

CROSS-REFERENCE TO RELATED APPLICATION

This application is the 35 U.S.C. § 371 national stage application of PCT Application No. PCT/US2020/026113, entitled "Method For Detecting Radiological Progression In Cancer Surveillance", filed Apr. 1, 2020, where the PCT claims priority to U.S. Provisional Application No. 62/828,239, entitled "Method For Detecting Radiological Progression In Cancer Surveillance" filed on Apr. 2, 2019, and to U.S. Provisional Application No. 62/828,871, entitled "Method For Detecting Radiological Progression In Cancer Surveillance" filed on Apr. 3, 2019 the entireties of which are herein incorporated by reference.

STATEMENT REGARDING FEDERALLY SPONSORED RESEARCH OR DEVELOPMENT

This invention was made with government support under grant number ECCS1903466 awarded by the National Science Foundation. The government has certain rights in the invention.

BACKGROUND

Low-grade gliomas cause significant neurological morbidity by brain invasion. There is currently no universally accepted objective technique available for detection of enlargement of low-grade gliomas in the clinical setting and subjective evaluation by clinicians using visual comparison of longitudinal radiological studies is a gold standard. Accordingly, there is a need to address the aforementioned deficiencies and inadequacies.

SUMMARY

One aspect of the disclosure, therefore, encompasses embodiments of a method for determining tumor status in a subject, the method comprising the steps of: (a) obtaining a first determination of the volume of a tumor in a human or animal subject; (b) obtaining a plurality of sectional images of the tumor in the human or animal subject after a period from step (a); (c) computing a second volume of the tumor from a plurality of sectional images from the subject; (d) determining the extent of tumor increase by comparing the first determination of the volume of the tumor from step (a) with the determination of the tumor volume in step (c) by applying an online abrupt change-of-point method to the plurality of sectional images; and (e) modifying a treatment protocol of the human or animal patient to reduce at least one of (i) the rate of increase of the tumor volume and (ii) the volume of the tumor.

In some embodiments of this aspect of the disclosure, the tumor can be a solid tumor.

In some embodiments of this aspect of the disclosure, the plurality of sectional images from the subject can be generated with an imaging scanner.

In some embodiments of this aspect of the disclosure, the plurality of sectional images can be magnetic resonance images, positron emission tomography images, or computer tomography images.

In some embodiments of this aspect of the disclosure, in step (b) the human or animal subject can be administered a contrast agent that enhances the plurality of images of the tumor.

In some embodiments of this aspect of the disclosure, the tumor can be a tumor of the brain.

In some embodiments of this aspect of the disclosure, the tumor can be an oligodendroglioma or an astroglioma.

Another aspect of the disclosure encompasses embodiments of a system for determining tumor status in a subject, the system comprising a computing device and logic stored on a non-transitory computer-readable media, wherein the logic, when executed by the computing device, generates a determination of the volume of a tumor in a patient from a plurality of sectional images of the tumor.

In some embodiments of this aspect of the disclosure, the system can further comprise an imaging scanner operably coupled to the computing device, and wherein the imaging scanner can generate the plurality of sectional images of the tumor in the human or animal subject.

In some embodiments of this aspect of the disclosure, the imaging scanner can be an magnetic resonance imaging (MRI) scanner.

In some embodiments of this aspect of the disclosure, the devices of the system can be operably connected by at least one a wired coupling and a wireless coupling.

In some embodiments of this aspect of the disclosure, the system automatically generating a determination of the volume of a tumor in a patient can comprise a memory, a processing device, a plurality of input/output interfaces, a network interface, a display, a peripheral interface, and a mass storage, wherein each of these devices can be connected across a local data bus.

In some embodiments of this aspect of the disclosure, the system can further comprise a peripheral measurement device connected to the system via the peripheral interface.

In some embodiments of this aspect of the disclosure, the memory can be selected from a random-access memory (RAM) or a non-volatile memory element.

In some embodiments of this aspect of the disclosure, the memory can comprise a native operating system, at least one native application, an emulation system or emulated application for at least one operating system, an emulated hardware platform, or an emulated operating systems.

In some embodiments of this aspect of the disclosure, the display can be selected from a computer monitor, a plasma screen for a PC, and a liquid crystal display (LCD).

In some embodiments of this aspect of the disclosure, the computer-readable medium can be selected from the group consisting of: a portable computer diskette, a random access memory (RAM), a read-only memory (ROM), an erasable programmable read-only memory (EPROM, EEPROM, or Flash memory), and a portable compact disc read-only memory (CDROM) (optical).

In some embodiments of this aspect of the disclosure, the network interface device can comprise a device that can communicate with both inputs and outputs and selected from the group consisting of a modulator/demodulator, a wireless transceiver, a telephonic interface, a bridge, a router, and a network card.

In some embodiments of this aspect of the disclosure, the system further comprises a mass storage.

BRIEF DESCRIPTION OF DRAWINGS

Many aspects of the disclosed devices and methods can be better understood with reference to the following drawings.

The components in the drawings are not necessarily to scale, emphasis instead being placed upon clearly illustrating the relevant principles. Moreover, in the drawings, like reference numerals designate corresponding parts throughout the several views.

FIGS. 1A and 1B show a plot of the tumor volumes of two patients in the clinical progression group, diagnosed with oligodendroglioma.

FIGS. 1C and 1D show a plot of the tumor volumes of two patients in the clinically-stable group diagnosed with an oligodendroglioma and an astroglioma, respectively. The volumes at the time-to-growth detected by computer-assisted-diagnosis (CAD) and visual comparison are colored in yellow and red, respectively.

FIGS. 1E and 1F show a plot of the tumor volumes of two patients with stable disease by CAD and visual comparison, diagnosed with an astroglioma and an oligodendroglioma, respectively. The x-axis corresponds to the time interval from the baseline MRI.

FIG. 1G plots the results of simulations of the mathematical model for grade 2 gliomas showing percent of brain invaded by the tumor (y-axis) as a function of the parameter for mitotic rate (/hr, colors) in the presence of a low angiogenesis rate (0.1/hr) (Scribner et al., (2017) *J. Neurooncol.* 133: 377-388).

FIG. 1H shows a curve fit of the normalized data of 14 patients with nonlinear growth using the model $f(x)=a*exp(b*x)$, coefficients (with 95% confidence bounds): a=0.03751 (0.02759, 0.04743), b=2.98 (2.691, 3.27), sse: 1.3701, R-square: 0.8580.

FIGS. 2A-2H illustrate the time-to-growth detected by computer-assisted-diagnosis methods of the disclosure and a visual comparison.

FIGS. 2A-2C are axial FLAIR MRIs of a patient in the clinical progression group, diagnosed with an oligodendroglioma, whose tumor volumes are shown in FIG. 1B, at baseline (FIG. 2A), the time-to-growth detected by computer-assisted-diagnosis (FIG. 2B), and visual comparison (FIG. 2C).

FIGS. 2D-2F show axial FLAIR MRIs of a clinically-stable patient diagnosed with a grade 2 oligodendroglioma, whose tumor volumes are shown in FIG. 1C, at baseline (FIG. 2D), the time-to-grow detected by computer-assisted-diagnosis (FIG. 2E), and the last follow-up MRI, considered to be stable by visual comparison (FIG. 2F). A visual review agreed that the tumor had grown. This patient elected to have a resection; the pathological diagnosis a revealed grade 3 oligodendroglioma.

FIGS. 2G and 2H show axial FLAIR MRIs of a clinically-stable patient diagnosed with an astroglioma, whose tumor volumes are shown in FIG. 1D, at baseline (FIG. 2G) and the time-to-growth detected by computer-assisted-diagnosis (FIG. 2H).

FIGS. 3A-3J illustrate growth away from the largest tumor section.

FIGS. 3A-3E show the MRIs of tumor 4385 at time 0.

FIGS. 3F-3J show the MRIs at the time of growth detected by CAD. The tumor exhibits growth in the third dimension away from the section containing the largest tumor (i.e. FIGS. 3A and 3F). The second MRI was deemed stable by visual comparison.

FIG. 8 illustrates Table 1 showing a summary of the MRI data. Interval to last MRI refers to the interval of time from the baseline MRI to the most recent MRI. CAD Dx and VC Dx refers to the determination of growth or not (i.e. stable) by the computer assisted diagnostic method (CAD) of the disclosure or visual comparison (VC), respectively. Time 1 denotes the time CAD detects growth at a time earlier than the last MRI, if any. Groups 1, 2, and 3 refer to patients with known radiological tumor progression, stable glioma, and imaging abnormality, respectively. As compared to VC, CAD detected earlier growth in 29 group 1 gliomas and 13 group gliomas.

DETAILED DESCRIPTION

Figure 1A:
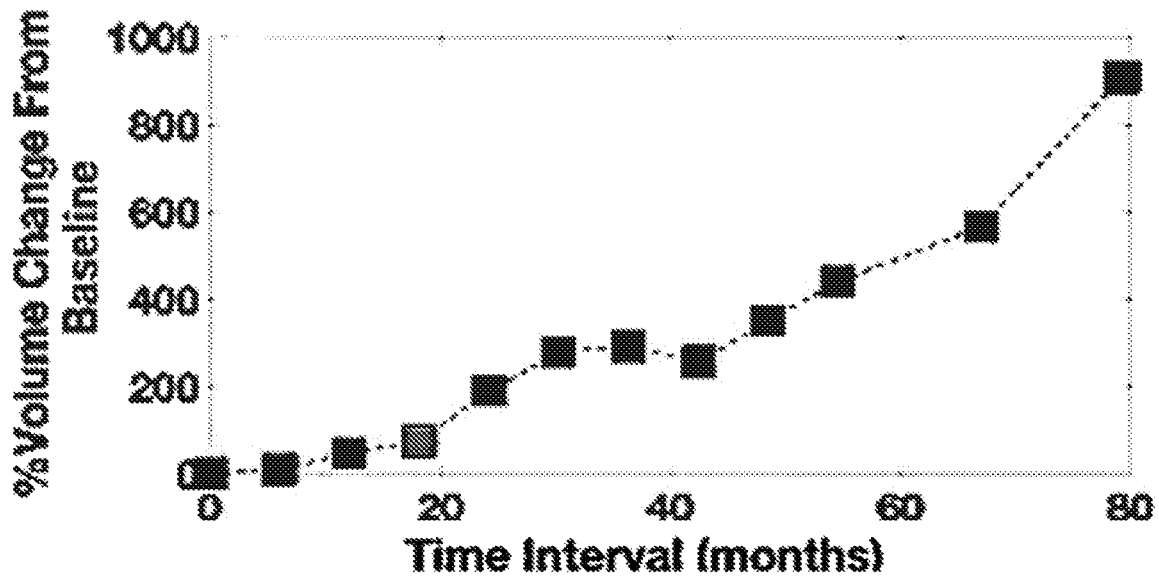
FIGS. 1A-1H illustrate growth curves of grade 2 gliomas.
Figure 1C:
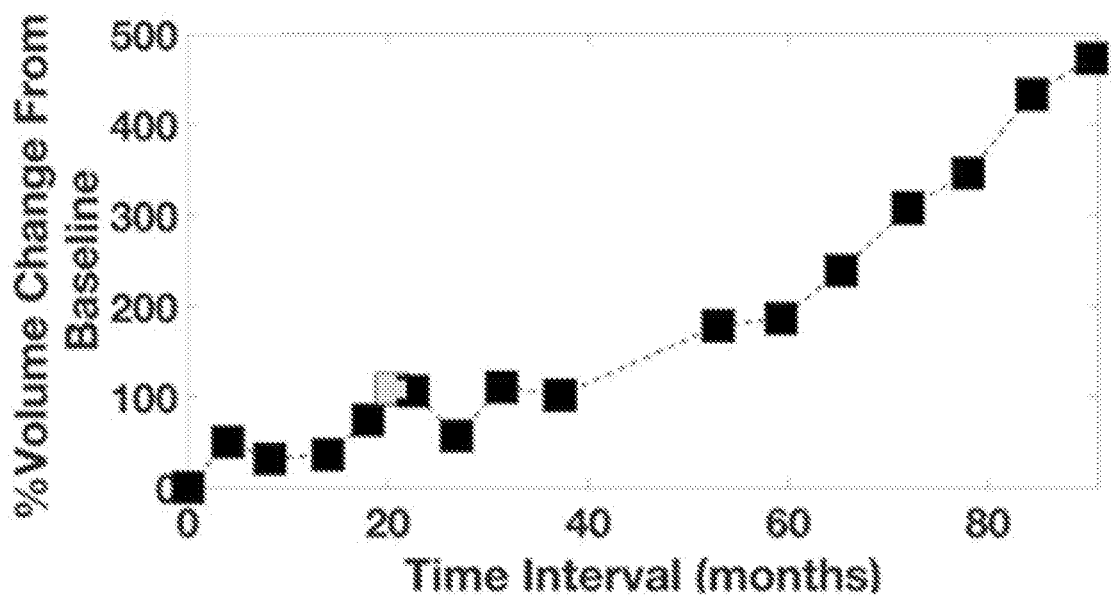
Figure 1B:
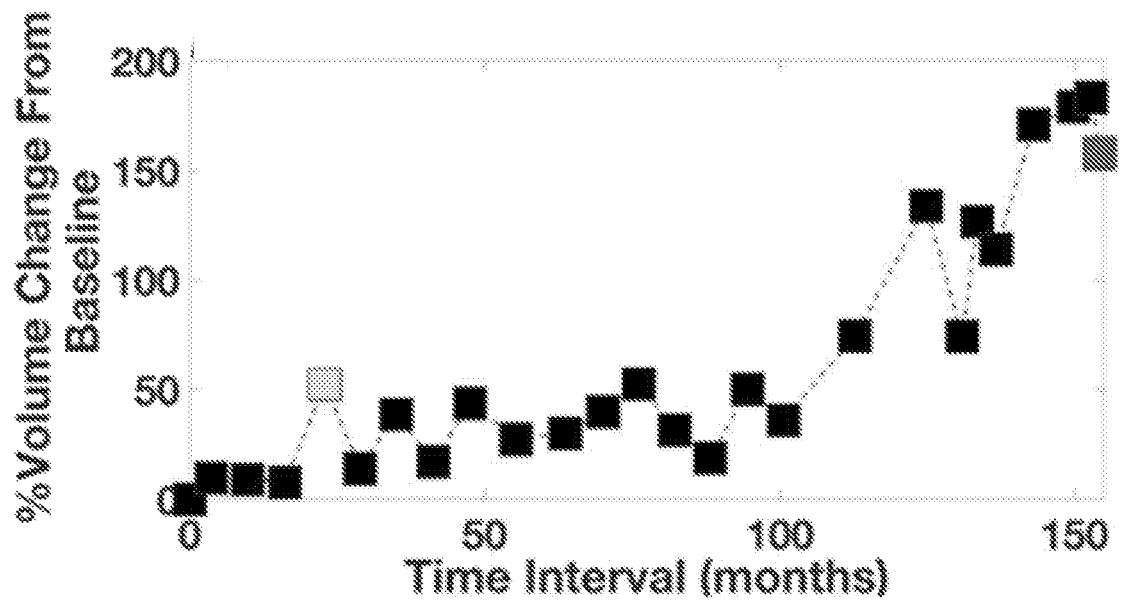
Figure 1D:
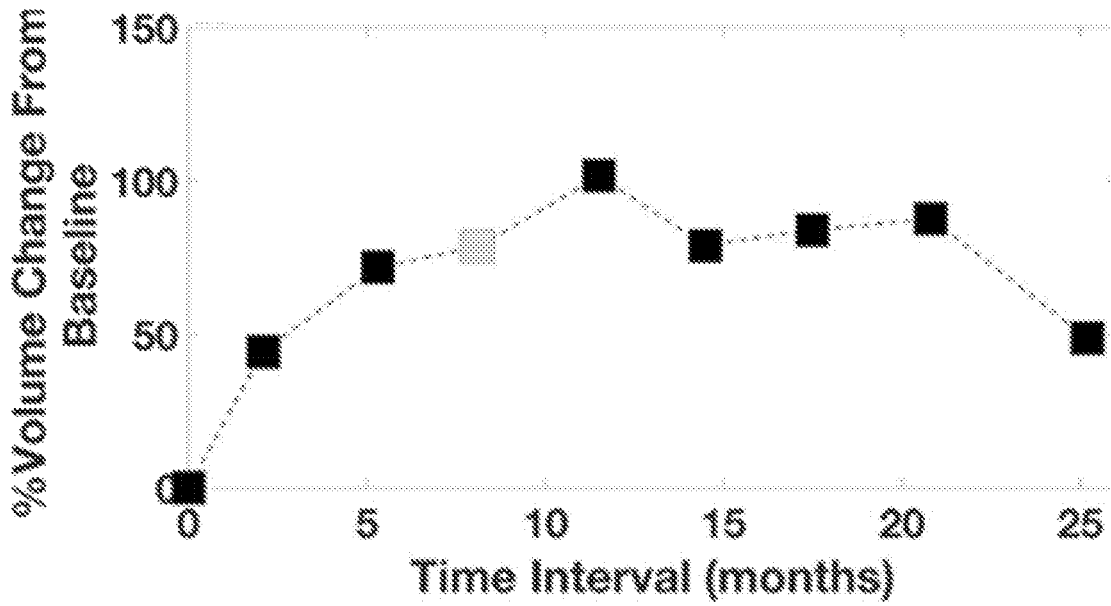

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

The term "cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

The term "oligodendroglioma" as used herein refers to type of glioma believed to originate from the oligodendrocytes of the brain or from a glial precursor cell. They occur primarily in adults but are also found in children. They occur mainly in the frontal lobe. A computed tomography (CT) or magnetic resonance imaging (MRI) scan is necessary to characterize the anatomy of this tumor (size, location, hetero/homogeneity). However, final diagnosis of this tumor, like most tumors, relies on histopathologic examination (biopsy examination). Although the tumor may appear to be vaguely circumscribed, it is by definition a diffusely infiltrating tumor.

Classically they tend to have a vasculature of finely branching capillaries that may take on a "chicken wire" appearance. When invading grey matter structures such as cortex, the neoplastic oligodendrocytes tend to cluster around neurons exhibiting a phenomenon referred to as "perineuronal satellitosis". Oligodendrogliomas may invade preferentially around vessels or under the pial surface of the brain. Oligodendrogliomas must be differentiated from the more common astrocytoma. Non-classical variants and combined tumors of both oligodendroglioma and astrocytoma differentiation are seen, making this distinction controversial between different neuropathology groups. Other glial and glioneuronal tumors with which they are often confused due to their monotonous round cell appearance include pilocytic astrocytoma, central neurocytoma, the so-called dysembryoplastic neuroepithelial tumor, or occasionally ependymoma. Oligodendrogliomas are generally dichotomized into grade II (low grade) tumor. The ultimate responsibility for making treatment decisions and interpretation of these diagnose lies with the oncologist in consultation with the patient and their family.

By far, the most common structural deformity found is co-deletion of chromosomal arms 1p and 19q. The high frequency of co-deletion is a striking feature of this glial tumor and is considered as a "genetic signature" of oligodendroglioma. Allelic losses on 1p and 19q, either separately or combined, are more common in classic oligodendrogliomas than in either astrocytomas or oligoastrocytomas.

Oligodendrogliomas are generally felt to be incurable using current treatments. However compared to the more common astrocytoma, they are slow growing with prolonged survival. In one series, median survival times for oligodendrogliomas were 11.6 years for grade II. Because of the indolent nature of this tumor and the potential morbidity associated with neurosurgery, chemotherapy, and radiation therapy, most neurooncologists will initially pursue a course of watchful waiting and treat patients symptomatically.

Symptomatic treatment often includes the use of anticonvulsants for seizures and steroids for brain swelling.

Because of their diffusely infiltrating nature, oligodendrogliomas cannot be completely resected and are not curable by surgical excision. If the tumor mass compresses adjacent brain structures, a neurosurgeon will typically remove as much of the tumor as possible without damaging other critical, healthy brain structures. Surgery may be followed up by chemotherapy, radiation, or a mix of both, but recent studies suggest that radiation does not improve overall survival.

Oligodendrogliomas, like all other infiltrating gliomas, have a very high (almost uniform) rate of recurrence and gradually increase in grade over time. Recurrent tumors are generally treated with more aggressive chemotherapy and radiation therapy. Recently, stereotactic surgery has proven successful in treating small tumors that have been diagnosed early. Long-term survival is reported in a minority of patients. With aggressive treatment and close monitoring, it is possible to outlive the typical life expectancies for low grade oligodendroglioma.

The term "astrocytoma" as used herein refers to a type of brain tumor. They originate in a particular kind of glial cells, star-shaped brain cells in the cerebrum called astrocytes. This type of tumor does not usually spread outside the brain and spinal cord and it does not usually affect other organs. Astrocytomas are the most common glioma and can occur in most parts of the brain and occasionally in the spinal cord. Within the astrocytomas, two broad classes are recognized in literature, those with: (i) Narrow zones of infiltration (mostly noninvasive tumors; e.g., pilocytic astrocytoma, subependymal giant cell astrocytoma, pleomorphic xanthoastrocytoma), that often are clearly outlined on diagnostic images, or (ii) diffuse zones of infiltration (e.g., high-grade astrocytoma, anaplastic astrocytoma, glioblastoma), that share various features, including the ability to arise at any location in the central nervous system, but with a preference for the cerebral hemispheres. The low-grade type is more often found in children or young adults, while the high-grade type is more prevalent in adults. Astrocytomas in the base of the brain are more common in young people and account for roughly 75% of neuroepithelial tumors.

An X-ray computed tomography (CT) or magnetic resonance imaging (MRI) scan is necessary to characterize the extent of these tumors (size, location, consistency). CT will usually show distortion of third and lateral ventricles with displacement of anterior and middle cerebral arteries. Histologic analysis is necessary for grading diagnosis. In the first stage of diagnosis the doctor will take a history of symptoms and perform a basic neurological exam, including an eye exam and tests of vision, balance, coordination and mental status. The doctor will then require a CT scan and MRI of the patient's brain. During a CT scan, X-rays of the patient's brain are taken from many different directions. These are then combined by a computer, producing a cross-sectional image of the brain. For an MRI, the patient relaxes in a tunnel-like instrument while the brain is subjected to changes of magnetic field. An image is produced based on the behavior of the brain's water molecules in response to the magnetic fields. A special dye or contrast agent may be injected into a vein before these scans to provide contrast and make tumors easier to identify.

If a tumor is found, a neurosurgeon must perform a biopsy on it. This simply involves the removal of a small amount of tumor tissue, which is then sent to a neuropathologist for examination and grading. The biopsy may take place before surgical removal of the tumor or the sample may be taken during surgery. Grading of the tumor sample is a method of classification that helps the doctor to determine the severity of the astrocytoma and to decide on the best treatment options. The neuropathologist grades the tumor by looking for atypical cells, the growth of new blood vessels, and for indicators of cell division called mitotic figures.

A four-tiered histologic grading guideline for astrocytomas assigns a grade from 1 to 4, with 1 being the least aggressive and 4 being the most aggressive.

For low-grade astrocytomas, removal of the tumor generally allows functional survival for many years. In some reports, the 5-year survival has been over 90% with well-resected tumors. Indeed, broad intervention of low-grade conditions is a contested matter. In particular, pilocytic astrocytomas are commonly indolent bodies that may permit normal neurologic function. However, left unattended, these tumors may eventually undergo neoplastic transformation. To date, complete resection of high-grade astrocytomas is impossible because of the diffuse infiltration of tumor cells into normal parenchyma. Thus, high-grade astrocytomas inevitably recur after initial surgery or therapy, and are usually treated similarly as the initial tumor.

The term "computed tomography" (CT) as used herein refers to a computerized x-ray imaging procedure in which a narrow beam of x-rays is aimed at a patient and quickly rotated around the body, producing signals that are processed by the machine's computer to generate cross-sectional images ("slices") of the body. These slices are called tomographic images and contain more detailed information than conventional x-rays. Once a number of successive slices are collected by the machine's computer, they can be digitally "stacked" together to form a three-dimensional image of the patient that allows for easier identification and location of basic structures as well as possible tumors or abnormalities.

The term "Magnetic Resonance Imaging" (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 (about 20 min), nitrogen-13 (about 10 min), oxygen-15 (about 2 min), and fluorine-18 (about 110 min). PET technology can be used to trace the biologic pathway of any compound in living humans (and many other species as well), provided it can be radiolabeled with a PET isotope. The half-life of fluorine-18 is long enough such that fluorine-18 labeled radiotracers can be manufactured commercially at an offsite location.

The terms "subject", "individual", or "patient" as used herein are used interchangeably and refer to an animal preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. In a particular embodiment, the mammal is a human. In other embodiments, animals can be treated; the animals can be vertebrates, including both birds and mammals. In aspects of the disclosure, the terms include domestic animals bred for food or as pets, including equines, bovines, sheep, poultry, fish, porcines, canines, felines, and zoo animals, goats, apes (e.g. gorilla or chimpanzee), and rodents such as rats and mice.

The term "contrast agent" as used herein refers to an agent that when delivered to an animal or human subject can improve the image obtained by a method such as magnetic resonance imaging (MRI). Such agents may include, but are not limited to gadolinium, iron oxide, manganese and magnesium salts, and the like that may be formulated into pharmaceutically acceptable compositions for administering in vivo with limited and acceptable degrees of undesirable side effects. One suitable MRI contrast agent for incorporation into the liposomal nanoparticle delivery vehicles of the disclosure is gadolinium (Gd), and derivatized variants thereof. Other contrast agents may be selected by one of skill in the art for a particular imaging method other than MRI.

Discussion

Described herein are systems and methods relating to computer-assisted-diagnostics (CAD) for cancer that are advantageous for determining a tumor progression, thereby allowing administered treatment protocols to be modified to prolong the life of a patient in need and/or to reduce or eliminate the viability of the tumor. In certain aspects, systems and methods as described herein can aid physicians in detecting earlier growth of cancers, for example low-grade gliomas.

Systems and methods as described herein provide for improvements in existing systems and methods for detecting radiological progression of cancer. Systems and methods as described herein can be used to improve the accuracy of detection of cancer progression, leading to earlier diagnosis and modified treatment protocols. Systems and methods as described herein can be used to monitor and measure tumor progression in a subject (which can be a human, mammal, or other living subject having cancer of a part of the body), or can be used to retrospectively monitor images acquired from apparatuses as described herein.

Methods as described herein can comprise segmentation of images, computing volumes of tumors in the images or segmented images, and identifying changes in growth by the application of the online abrupt change-of-point method. Methods as described herein can further incorporate visual reviewing of tumor margins (from the images or segmented images), such as, but not limited to, a trained physician. Methods as described herein can further comprise the determination of tumor status (for example, whether a growing or stable tumor) by one or more visual reviewers based upon the segmented images, computed volumes, and statistical results. Methods as described herein can further comprise comparing diagnostic results to retrospective review of radiological reports.

Methods as described herein can further comprise positioning a subject in relation to an imaging scanner, for example an MRI scanner, collecting images, and using additional aspects of methods as described herein on the collected images. Methods as described herein can further comprise outputting a disease status, such as a tumor status, to a display (for example a computer display operably connected to or part of the computing devices as described herein).

Systems as described herein can incorporate computing devices, and instructions that embody methods of the present disclosure stored as executable logic on one or more non-transitory media of the computing device. Systems as described herein can further comprise imaging scanners, for example a magnetic resonance imaging (MRI) scanner such as those known in the art.

Figure 6:
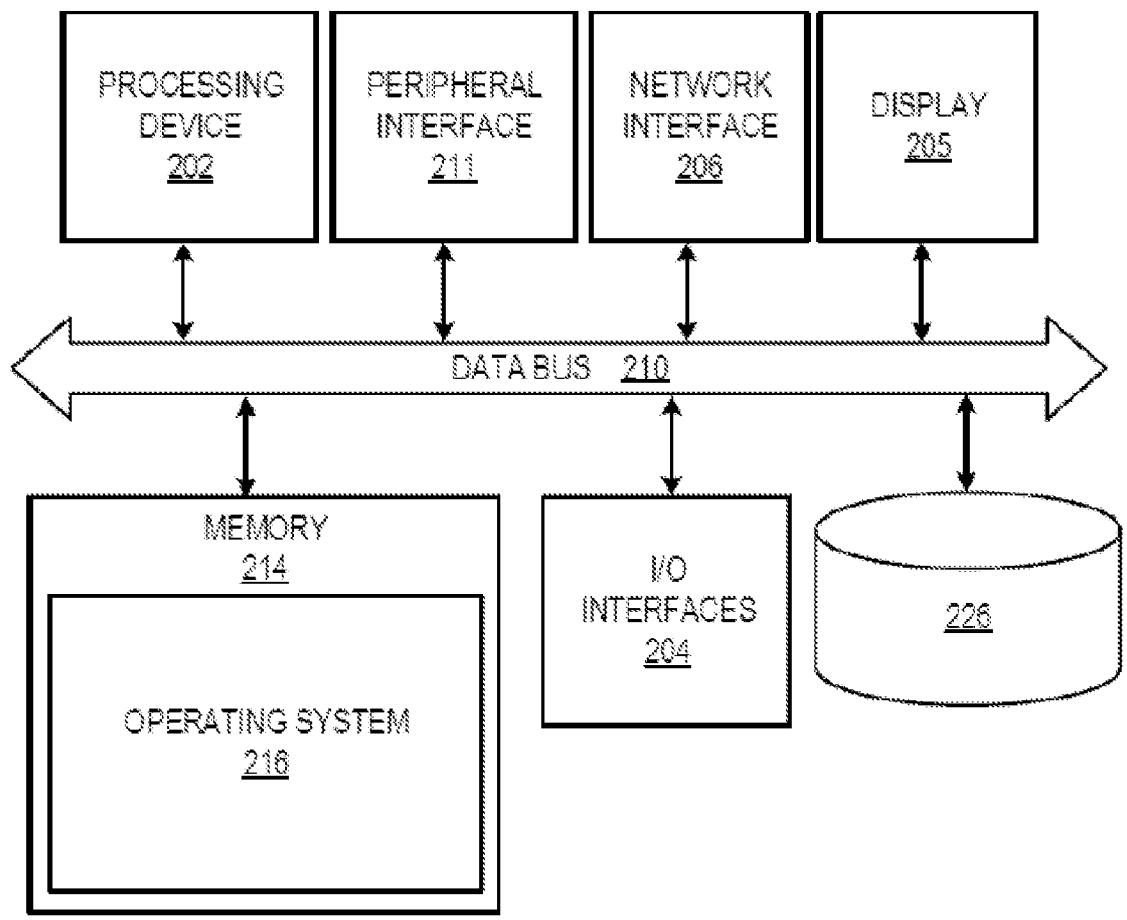
FIG. 6 shows an embodiment of a computing device or apparatus 1010 that can be implemented in the systems as described herein and which can implement methods as described herein.

Referring now to FIG. 6, depicted is an apparatus 1010 in which the systems, or other systems described herein may be coupled to assist in automation of the system. The apparatus 1010 can be embodied in any one of a wide variety of wired and/or wireless computing devices, multiprocessor computing device, and so forth. As shown in FIG. 6, the apparatus 1010 comprises a memory 214, a processing device 202, a plurality of input/output interfaces 204, a network interface 206, a display 205, a peripheral interface 211, and mass storage 226, wherein each of these devices can be connected across a local data bus 210. The apparatus 1010 can be coupled to one or more peripheral measurement devices (not shown) connected to the apparatus 1010 via the peripheral interface 211.

The processing device 202 can include any custom-made or commercially-available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications can include application specific software which may be configured to perform some or all of the methods described herein (Labview, for example). In accordance with such embodiments, the application specific software is stored in memory 214 and executed by the processing device 202. One of ordinary skill in the art will appreciate that the memory 214 can, and typically will, comprise other components which have been omitted for purposes of clarity.

Input/output interfaces 204 provide any number of interfaces for the input and output of data. For example, where the apparatus 1010 comprises a personal computer, these components may interface with one or more user input devices 204. The display 205 can comprise a computer monitor, a plasma screen for a PC, a liquid crystal display (LCD) on a handheld device, or other display device.

In the context of this disclosure, a non-transitory computer-readable medium stores programs for use by or in connection with an instruction execution system, apparatus, or device. More specific examples of a computer-readable medium can include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 6, a network interface device 206 comprises various components used to transmit and/or receive data over a network environment. For example, the network interface 206 can include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 can communicate with one or more computing devices via the network interface 206 over a network. The apparatus 1010 may further comprise mass storage 226. The peripheral 211 interface supports various interfaces including, but not limited to IEEE-1394 High Performance Serial Bus (Firewire), USB, thunderbolt, a serial connection, and a parallel connection.

The apparatus 1010 shown in FIG. 6 can be embodied, for example, as a magnetic resonance apparatus, which includes a processing module or logic for performing conditional data processing, and may be implemented either off-line or directly in a magnetic resonance apparatus. For such embodiments, the apparatus 1010 can be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and U.S. Publication No. 2011/0181285, which are incorporated by reference as if fully set forth herein.

Figure 7:
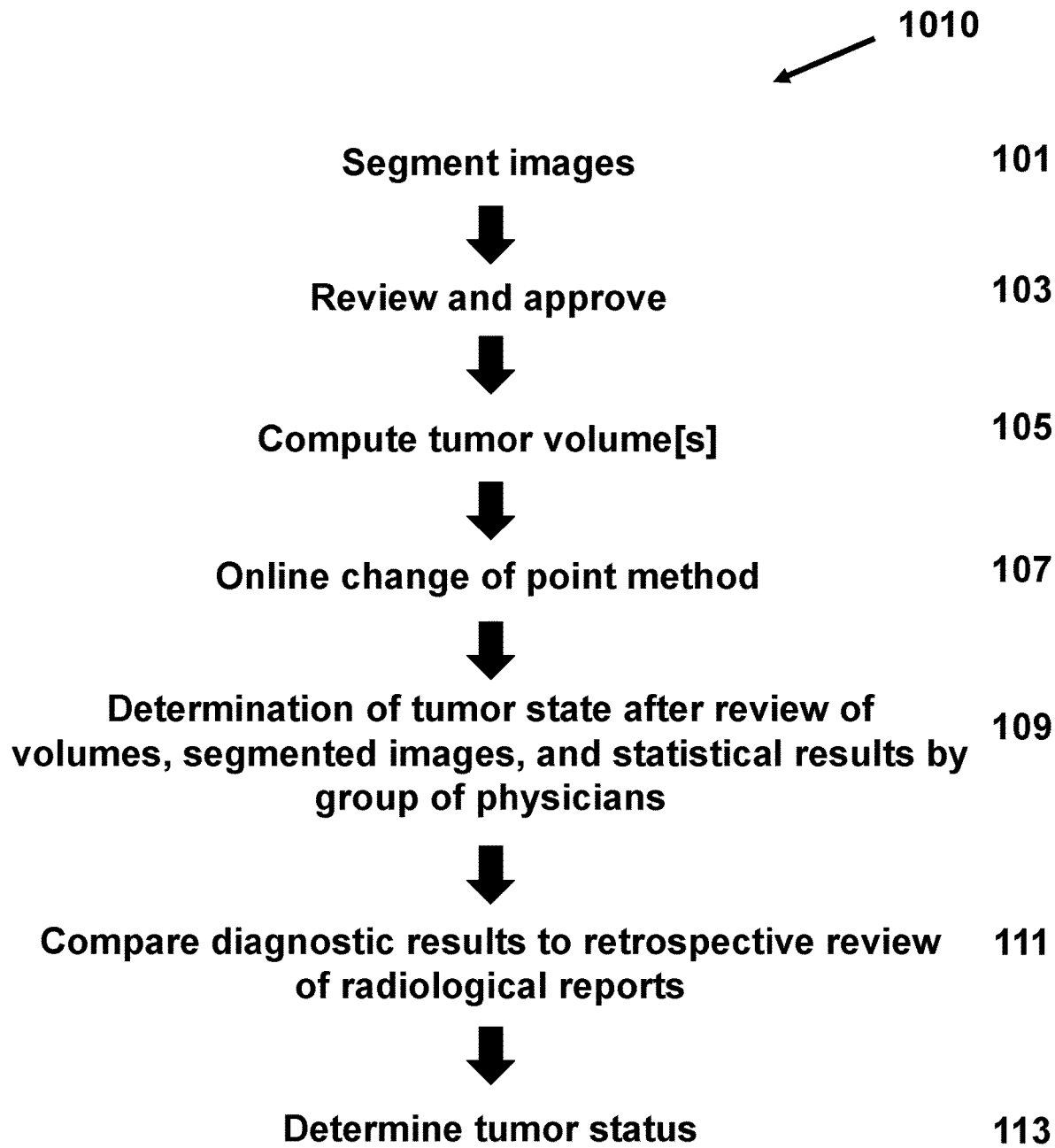
FIG. 7 is an embodiment of a method according to the present disclosure.

Referring now to the flow charts of FIG. 7, shown is an example of functionality that can be implemented in the apparatus 1010 of FIG. 6. If embodied in software, certain blocks shown in FIG. 7 can represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 6) in a computer system or other system. The machine code can be converted from the source code, etc. If embodied in hardware, each block may represent a circuit or a number of interconnected circuits to implement the specified logical function(s).

Although the flowchart of FIG. 7 shows a specific order of execution, it is understood that the order of execution may differ from that which is depicted. For example, the order of execution of two or more blocks may be scrambled relative to the order shown. Also, two or more blocks shown in succession in FIG. 7 can be executed concurrently or with partial concurrence. Further, in some embodiments, one or more of the blocks shown in FIG. 7 can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

As further described in Example 1 below, the tumors of 63 subjects in 627 MRI were digitized, including 34 grade 2 gliomas with radiological progression, 22 radiologically stable grade 2 gliomas, and 7 patients with non-specific imaging abnormality. None received radiation therapy. The 56 patients with gliomas included 30 males and 26 females with a mean age of 48 and a range of follow-up of 150.2 months. The CAD method of the disclosure comprises of tumor segmentation, computing volumes, and pointing to growth by the online abrupt change-of-point method, which considers only past measurements. Independent visual reviewers evaluated the segmentation method. Seven reviewers reviewed the CAD predictions to determine the time of growth. In 29 of the 34 subjects with progression, the median time-to-growth detection was only 14 months for CAD compared to 44 months for current standard of care radiological evaluation (p=4e−9). Using the CAD method of the disclosure, accurate detection of tumor enlargement was possible with a median of only 57% change in the tumor volume as compared to a median of 174% change of volume necessary to diagnose tumor growth using current standard of care clinical methods (p=7e−8). In the radiologically-stable group, CAD facilitated growth detection in 13 out of 22 patients. CAD did not detect growth in the imaging abnormality group.

One aspect of the disclosure, therefore, encompasses embodiments of a method for determining tumor status in a subject, the method comprising the steps of: (a) obtaining a first determination of the volume of a tumor in a human or animal subject; (b) obtaining a plurality of sectional images of the tumor in the human or animal subject after a period from step (a); (c) computing a second volume of the tumor from a plurality of sectional images from the subject; (d) determining the extent of tumor increase by comparing the first determination of the volume of the tumor from step (a) with the determination of the tumor volume in step (c) by applying an online abrupt change-of-point method to the plurality of sectional images; and (e) modifying a treatment protocol of the human or animal patient to reduce at least one of (i) the rate of increase of the tumor volume and (ii) the volume of the tumor.

In some embodiments of this aspect of the disclosure, the tumor can be a solid tumor.

In some embodiments of this aspect of the disclosure, the plurality of sectional images from the subject can be generated with an imaging scanner.

In some embodiments of this aspect of the disclosure, the plurality of sectional images can be magnetic resonance images, positron emission tomography images, or computer tomography images.

In some embodiments of this aspect of the disclosure, in step (b) the human or animal subject can be administered a contrast agent that enhances the plurality of images of the tumor.

In some embodiments of this aspect of the disclosure, the tumor can be a tumor of the brain.

In some embodiments of this aspect of the disclosure, the tumor can be an oligodendroglioma or an astroglioma.

Another aspect of the disclosure encompasses embodiments of a system for determining tumor status in a subject, the system comprising a computing device and logic stored on a non-transitory computer-readable media, wherein the logic, when executed by the computing device, generates a determination of the volume of a tumor in a patient from a plurality of sectional images of the tumor.

In some embodiments of this aspect of the disclosure, the system can further comprise an imaging scanner operably coupled to the computing device, and wherein the imaging scanner can generate the plurality of sectional images of the tumor in the human or animal subject.

In some embodiments of this aspect of the disclosure, the imaging scanner can be an magnetic resonance imaging (MRI) scanner.

In some embodiments of this aspect of the disclosure, the devices of the system can be operably connected by at least one a wired coupling and a wireless coupling.

In some embodiments of this aspect of the disclosure, the system automatically generating a determination of the volume of a tumor in a patient can comprise a memory, a processing device, a plurality of input/output interfaces, a network interface, a display, a peripheral interface, and a mass storage, wherein each of these devices can be connected across a local data bus.

In some embodiments of this aspect of the disclosure, the system can further comprise a peripheral measurement device connected to the system via the peripheral interface.

In some embodiments of this aspect of the disclosure, the memory can be selected from a random-access memory (RAM) or a non-volatile memory element.

In some embodiments of this aspect of the disclosure, the memory can comprise a native operating system, at least one native application, an emulation system or emulated application for at least one operating system, an emulated hardware platform, or an emulated operating systems.

In some embodiments of this aspect of the disclosure, the display can be selected from a computer monitor, a plasma screen for a PC, and a liquid crystal display (LCD).

In some embodiments of this aspect of the disclosure, the computer-readable medium can be selected from the group consisting of: a portable computer diskette, a random access memory (RAM), a read-only memory (ROM), an erasable programmable read-only memory (EPROM, EEPROM, or Flash memory), and a portable compact disc read-only memory (CDROM) (optical).

In some embodiments of this aspect of the disclosure, the network interface device can comprise a device that can communicate with both inputs and outputs and selected from the group consisting of a modulator/demodulator, a wireless transceiver, a telephonic interface, a bridge, a router, and a network card.

In some embodiments of this aspect of the disclosure, the system further comprises a mass storage.

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

Example 1

Cancer patients are typically monitored with serial imaging of the affected organ; timely detection of tumor recurrence can have profound implications on morbidity and survival times. Low-grade gliomas (WHO grade 2) constitute 15% of all adult brain tumors (Rasmussen et al., (2017) *J. Neurooncol.* 135: 571-579; Berntsson et al., (2018) *J. Neurol.* 265: 1432-1442; Brainlesion (2018) *Glioma, Multiple Sclerosis, Stroke and Traumatic Brain Injuries.* Heinz, ed. Springer International Publishing). Patients diagnosed with low-grade gliomas are followed by serial magnetic resonance imaging (MRI) of the brain. The fluid-attenuated inversion-recovery (FLAIR) is the principle imaging sequence for assessment of growth of low-grade gliomas (Bynevelt et al., (2001) *Neuroradiology* 43: 129-133).

At initial diagnosis, low-grade gliomas may be treated either by surgery, with or without radiation and chemotherapy (Delgado-Lopez et al., (2017) *Clin. Transl. Oncol.* 19: 931-944; Buckner et al., (2017) *Nat. Rev. Neurol.* 13: 340-351; Le Rhun et al., (2016) *Curr. Neurol. Neurosci. Rep.* 16:15). Greater resections of low-grade gliomas are associated with improved overall survival time and progression-free survival time (Claus et al., (2005) *Cancer* 103:1227-1233; Johannesen et al., (2003) *J. Neurosurg.* 99: 854-862; McGirt et al., (2009) *J. Neurosurg.* 110: 156-162; Nakamura et al., (2000) *Oncology* 58: 108-116; Ahmadi et al., (2009) *Acta Neurochir.* (Wien) 151: 1359-1365; Smith et al., (2008) *J. Clin. Oncol.* 26: 1338-1345; Sanai & Berger (2008) *Neurosurgery* 62: 753-764). Low-grade gliomas may continue to grow as grade 2 gliomas or may transform to higher grades (Scribner et al., (2017) J. Neurooncol. 133: 377-388); furthermore, at the time of recurrence, they may also be treated either by surgery with or without radiation therapy and chemotherapy (Baumert et al., (2016) Lancet Oncol. 17: 1521-1532; Jhaveri et al., (2018) Cancer 124: 1169-1178).

At present, visual comparison of two-dimensional (2D) FLAIR images with or without bi-dimensional measurement is the best available method for surveillance of low-grade gliomas. Two-dimensional (2D) images from a series of longitudinal studies are compared. Because the overall survival time of a low-grade glioma is measured in years, most of the patients have a large longitudinal series of images for several years. Comparison of the current MRI with all prior imaging takes a significant time for image interpretation, which is practically not feasible in the current protocols. Furthermore, multiple physicians are involved in assessment of tumor growth introducing high inter-observer variability (Kerkhof et al., (2016) *Eur. J. Neurol.* 23: 1528-1533).

As described herein, a detection of a change in the state of the tumor, i.e. tumor growth, can be improved by a computer-assisted diagnostic procedure that digitizes the tumor and directs the attention of the physician to a change in volume. Aa small tumor size is associated with less neurological morbidity (Berntsson et al., (2018) *J. Neurol.* 265: 1432-1442; Reijneveld et al., (2016) *Lancet Oncol.* 17: 1533-1542) but the improved protocol of the disclosure allows a more rapid determination of necessary changes to the treatment protocol to more effectively benefit the patient in need.

Image segmentation and analysis are non-trivial problems because of the unpredictable appearance and shape of brain tumors on MRI. Recently, several artificial intelligence methods and configurations have been applied to brain diseases, including brain tumors (Wang et al., (2016) *Prog. Electromag. Res.* 156: 105-133). Described herein are embodiments of methods for image segmentation of medical images that extracts object boundaries by computer vision (Dera et al., (2016) *Bull. Math. Biol.* 78: 1450-1476). Methods as described herein apply non-negative matrix factorization and a modified level set method; they do not use deep learning, training data, or neural networks. Detection of abrupt changes in the characteristics of physical systems is a fundamental problem in signal processing; applications include fault detection and diagnosis, safety of aircrafts, prediction of earthquakes, and biomedical applications, like EEG, EMG, and ECG analysis (Brodsky (1993) *Nonparametric Methods in Change-Point Problems*: Springer, Netherlands; 1993; Killick & Eckley 2012) *J. Am. Statis. Assoc.* 107: 1590-1598).

Methods

Study Design: Aspects of the present disclosure represent a retrospective observational study of the accuracy of the diagnosis of growth by expert physicians who view MRIs in a clinical setting and by 7 expert physicians who, in addition, are provided segmented images, numerical volumes, and a statistical determination of growth by the change-of-point method. Patient Selection and Study Size: The range, mean and median of the follow-up were 150.2, 46.6 and 33.6 months, respectively. The inclusion criteria were: pathological diagnosis of grade 2 oligodendroglioma (oligo), grade 2 astrocytoma (astro), or grade 2 mixed glioma (mixed) in the brain excluding the pineal gland; at least 4 MRIs had to be available for review either after the initial diagnosis or after the completion of chemotherapy with temozolomide (if applicable). The exclusion criterion were: treatment with radiation therapy after the initial diagnosis; and radiological reports indicating development of new enhancement without an increase in FLAIR signal.

Patients treated by radiation therapy are excluded because radiation may confound the results by causing an independent increase in FLAIR signal. Patients whose radiological reports describe new enhancing nodules without an increase in FLAIR signal because were excluded because they are easily detected by visual examination.

A total of 56 patients met the inclusion criteria, including 19 oligodendroglioma, 26 astrogliomas and 11 mixed gliomas; only 2 patients received temozolomide (Table 2). All of the oligodendroglioma have the 1p/19q co-deletions except for one patient with a single deletion of 19q. At the time of initiation of this study, 34 of 56 patients had been diagnosed with clinical progression while the remaining 22 of 56 patients were diagnosed as being clinically-stable by visual comparison of the most recent MRI performed at the last clinic visit.

The records of 8 patients were reviewed followed in clinics for an imaging abnormality without pathological diagnosis; one patient was excluded for lack of follow-up information. All 7 patients were considered clinically stable at the time of this study. Tumor Segmentation: A total of 627 MRIs were analyzed. Segmentation of the FLAIR sequence can be performed by two procedures: 1) an automated method that classifies and contours the different regions in the image; it applies non-negative matrix factorization and a modified level set method (NMF-LSM) as detailed in Dera et al., ((2016) *Bull. Math. Biol.* 78: 1450-1476). This automated segmentation generates 8 segments for every image (see Dera et al., (2016) *Bull. Math. Biol.* 78: 1450-1476), which are ranked by their maximal intensities. 2) The final tumor margins were obtained by combining the regions whose maximal intensities were above the level of the gray matter. A physician can review and approve the final tumor margins. Detailed information on the segmentation method and combining the segments to compute tumor margins are presented elsewhere (Dera et al., (2016) In: Crimi et al., eds *Brain lesion: Glioma, Multiple Sclerosis, Stroke and Traumatic Brain Injuries*: Springer International Publishing pp 195-205). Organizers of the Multimodal Brain Tumor Segmentation (BraTS) challenge have independently evaluated the accuracy of this method in the segmentation of the hyper-intense areas in T2/FLAIR MRI (i.e. whole tumor label) (Bakas et al., (2018) *Progression Assessment, Overall Survival Prediction BRATS Challenge*).

Tumor volumes were computed by multiplying the sum of the tumor segments in all axial images by the distance between images.

Online Abrupt Changes of Point: To exclude FLAIR changes due to the evolution of post-surgical changes, the baseline volume in the longitudinal series is the first minimum after surgical resection. To identify an abrupt change of volume, the function findchangepts in Matlab was applied (Mathworks, MA), by detecting a change in the root-mean-square level at a minimum threshold of 500/(volume at baseline) and a minimum of 2 samples between change-points. The number 500 corresponds to 5% of the rounded median of the baseline volumes.

In the clinical setting, a physician reviews the current MRI and compares it to MRIs performed on earlier dates. To simulate a clinic visit, the online change-of-point considers only past measurements. The time-to-growth detected by the computer-assisted-diagnostic method corresponds to the period of time between the dates of the base line MRI and the first change of point.

Time-to-growth detected by standard clinical care: Longitudinal MRIs variable time frame were evaluated by different board-certified neuro-radiologists to generate the radiological reports. The time-to-growth from the impressions of the radiological reports of these subjects were retrospectively calculated.

Review of Growth Detection by The Change-of-Point Method: Growth detected by the statistical change-of-point method was reviewed by seven physicians board-certified in neuro-radiology, Society of Neuro-Imaging, neuro-oncology, radiation oncology, and neurosurgery. The physicians were provided with: 1) the tumor volumes, 2) determination of growth or stability by the change-of-point method, and 3) the images with segmentation of 63 cases obtained at: a) the baseline (as defined in the previous section), b) at the time of growth detected by the statistical change-of-point method, if different than the last visit, and c) at the most recent visit. The images included a red line contouring the tumor margins, delineated by the segmentation method. The physicians were asked to determine if the tumor had grown as compared to baseline or not. The reader has the option of reviewing these MRIs and volumes, including the segmentation data; Table 1 (FIG. 8) shows a summary of the data. Mathematical Model of Gliomas: A system of partial differential equations (PDE) that models gliomas growth at the scale of MRI and pathology have been recently reported. The equations include the rates of replication (mitosis), brain invasion, angiogenesis, and a threshold for hypoxia; the numerical methods used to solve the system of PDE are detailed elsewhere (Scribner et al., (2017) *J. Neurooncol.* 133: 377-388; Scribner et al., (2014) PLoS One. 9: e115018; Raman et al., (2016) PLoS One. 11: e0146617 [18, 28, 29]. Statistical Analysis and Curve Fitting: The p-values were generated by the Mann-Whitney-Wilcoxon 2-tail test. Curve fitting was done in Matlab using the fit function and the poly1 ($y=p1*x+p2$) and exp 1 ($y=a*exp(b*x)$) models. Normalized volumes were computed by subtracting the baseline and dividing by the most recent. Time intervals from baseline were normalized by dividing by the largest. To identify tumors with exponential model growth, a normalized curve was selected if its nonlinear sum of squares due to error (sse)<0.6*linear sse (0.6 is chosen as it yields an exponential model fit R-Square>0.85 for the normalized data of all the selected curves).

Results

Patient Description: The computer-assisted-diagnostic method is applied to the longitudinal MRIs of a total of 56 gliomas; the mean age and gender are shown in Table 2.

TABLE 2

Characteristics of the Patients

| Pathology | Number | Age (mean) | Male | Female | Temozolomide |
|---|---|---|---|---|---|
| Oligodendroglioma | 19 | 47 | 11 | 8 | 1 |
| Astrocytoma | 26 | 46 | 14 | 12 | 1 |
| Mixed Glioma | 11 | 53 | 5 | 6 | 0 |
| All | 56 | 48 | 30 | 26 | 2 |

There were 3 groups of patients: 34 grade 2 gliomas with a known clinical progression, 22 grade 2 gliomas who are clinically stable by visual comparison, and 7 patients with an imaging abnormality, who are also clinically stable by visual comparison. Patients in the clinical progression group include 7 oligodendroglioma, 18 astrogliomas, and 9 mixed gliomas (Table 3). The clinically stable tumor group includes 12 oligodendroglioma, 8 astrogliomas, and 2 mixed gliomas (Table 3).

TABLE 3

Clinical progression glioma group

| Pathology | N | ΔG | CAD-TTG (months) | CAD iqr (months) | VC-TTG (months) | VC iqr (months) | p-TTG | CAD ΔV | VC ΔV | p-ΔV |
|---|---|---|---|---|---|---|---|---|---|---|
| Oligo | 7 | 7 | 19 | 10 | 79 | 53 | $5e^{-4}$ | 52% | 163% | $1e^{-3}$ |
| Astro | 18 | 14 | 12 | 6 | 33 | 18 | $6e^{-5}$ | 50% | 155% | $1e^{-3}$ |
| Mixed | 9 | 8 | 16 | 10 | 56 | 39 | $6e^{-4}$ | 69% | 286% | $3e^{-4}$ |
| All | 34 | 29 | 14 | 10 | 44 | 38 | $4e^{-9}$ | 57% | 174% | $7e^{-8}$ |

ΔG: number of patients whose time-to-growth (TTG) detected by computer-assisted-diagnosis (CAD-TTG) is earlier than visual comparison (VC-TTG).
CAD iqr: IQR of the CAD-TTG.
VC iqr: IQR of the VC-TTG.
CAD ΔV: median percent change in tumor volumes from baseline at the CAD-TTG.
VC ΔV: median percent change in tumor volumes from baseline at the VC-TTG.
The p-values were generated by the Mann-Whitney-Wilcoxon 2-tail test.
The results of CAD were identical to VC in 5 patients.

Computer-Assisted-Diagnosis (CAD) points to earlier time-to-growth: In the clinical progression group, the median time-to-growth by visual comparison for the oligodendroglioma, astrogliomas, and mixed gliomas were 79 months, 33 months, and 56 months, respectively. Computer-assisted-diagnosis methods of the disclosure aided the physicians in detecting statistically-significant earlier time-to-growth in 7/7 oligodendroglioma (median=19 months), 4/18 astrogliomas (median=12 months), and 8/9 mixed gliomas (median: 16 months; Table 2). Furthermore, the tumor size was significantly larger when detected by standard of care radiological assessment as compared to computer-assisted-diagnosis with median values of 163% vs. 52%, 155% vs. 50%, 286% vs. 69% for oligodendroglioma, astrogliomas, and mixed gliomas, respectively (Table 3 and FIGS. 1A-1H, and 2A-2H).

Time-to-growth in clinically-stable grade 2 gliomas: In the clinically-stable grade 2 glioma group, computer-assisted-diagnosis aided the physicians in detecting growth in 7/12 oligodendroglioma, 4/8 astrogliomas, and 2/2 mixed gliomas; the median periods of follow-up were, respectively, 37 months and 19 months for the grade 2 gliomas that have exhibited growth or remained stable by the computer-assisted-diagnostic method (Table 4).

TABLE 4

Clinically-stable glioma group

| Pathology | N | CAD-G | CAD-TTG | CAD-TTG iqr | FU-G | FU-G iqr | FU-S | FU-S iqr | CAD ΔV | CAD ΔV iqr |
|---|---|---|---|---|---|---|---|---|---|---|
| Oligo | 12 | 7 | 15 | 13 | 81 | 63 | 19 | 10 | 51% | 52% |
| Astro | 8 | 4 | 12 | 7 | 22 | 5 | 18 | 44 | 78% | 62% |
| Mixed | 2 | 2 | 8 | 2 | 87 | 28 | N.A. | N.A. | 42% | 32% |
| All | 22 | 13 | 13 | 8 | 37 | 67 | 19 | 26 | 58% | 40% |

CAD-G: number of patients in the clinically-stable group whose tumors have been detected to have grown by computer-assisted-diagnosis. CAD-TTG: time-to-growth detected by computer-assisted-diagnosis (months). FU-G: median of the period of time of follow-up of the patients diagnosed with growth by computer-assisted-diagnosis (months). FU-S: median of the period of time of follow-up of the patients whose tumors are stable by computer-assisted-diagnosis (months). CAD ΔV: median percent change in tumor volumes from baseline at the CAD-TTG. N.A.: not applicable. The iqr refers to the interquartile range. A statistical analysis between CAD-TTG and VC-TTG is not applicable here because the latter is not known; nonetheless, the VC-TTG will be larger than the FU-G. The Mann-Whitney-Wilcoxon 2-tail test comparing the CAD-TTG and FU-G of all 13 patients yields p=3e−4. The results of CAD were identical to VC in 9 patients.

The median time-to-growth detected by the computer-assisted-diagnostic method for oligodendroglioma, astrogliomas, and mixed gliomas were 15 months, 12 months, and 8 months, respectively (Table 4).

Figure 2D:
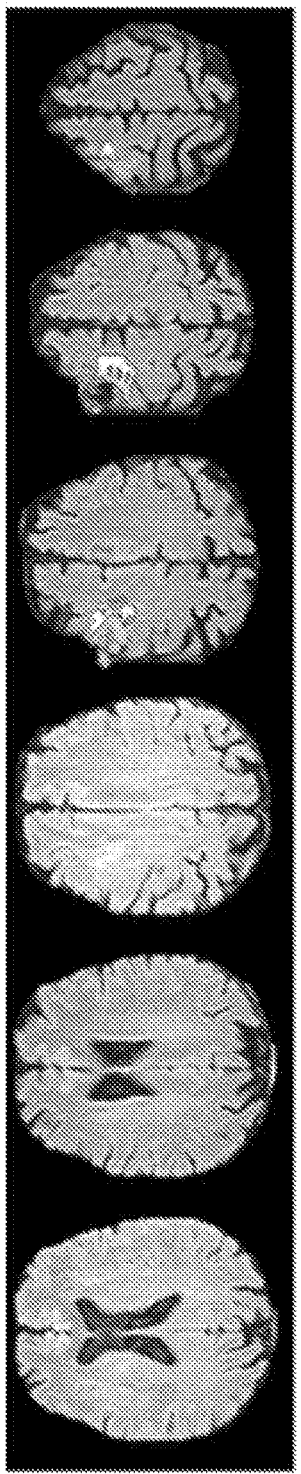
Figure 2E:
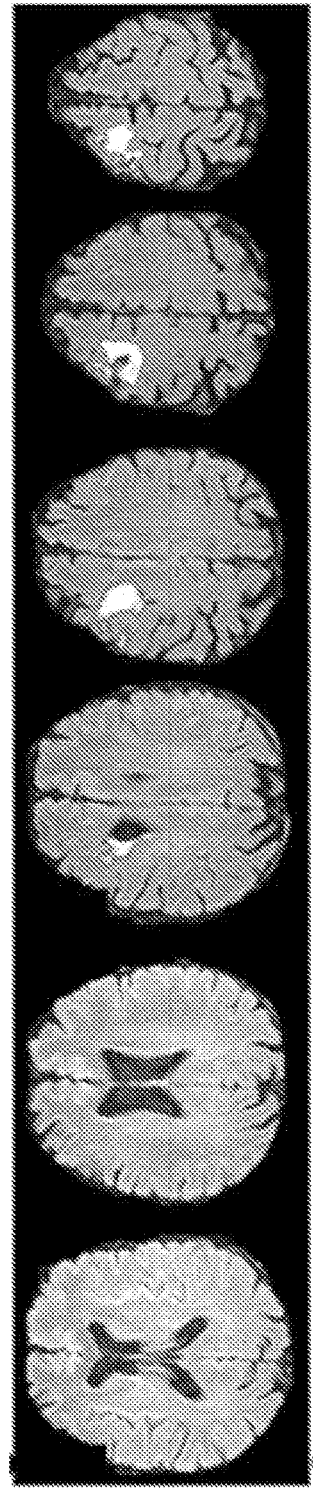
Figure 2F:
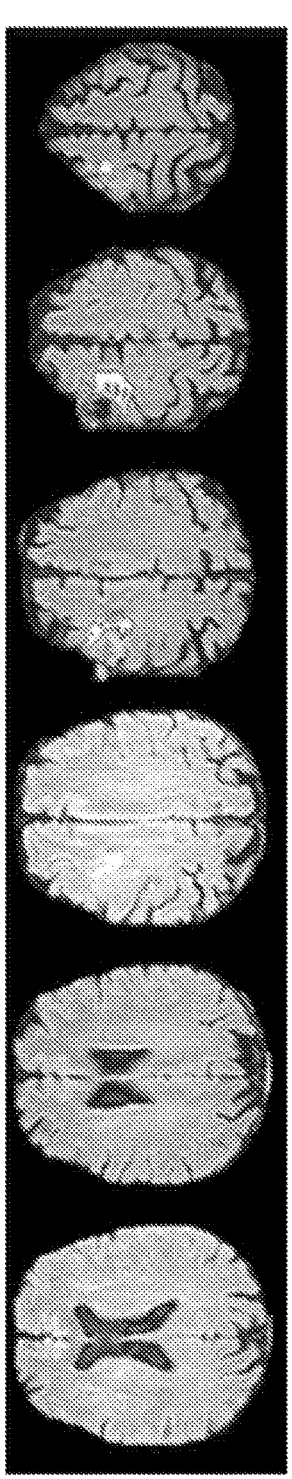
Figure 2G:
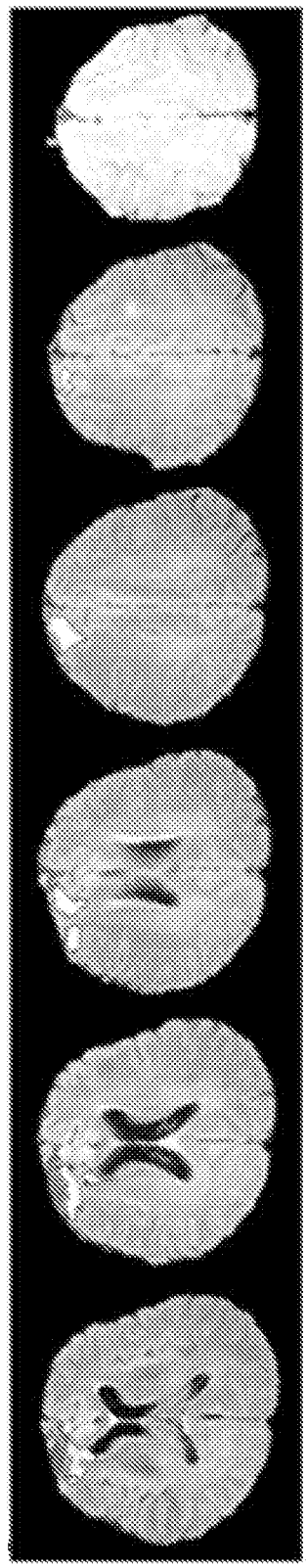
Figure 2H:
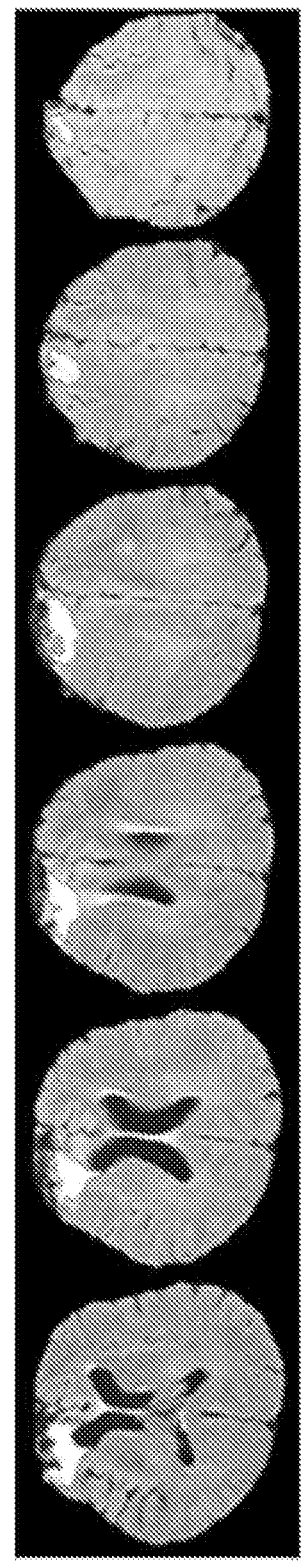

Three of these 13 gliomas exhibited additional tumor growth during the follow-up period after the time-to-growth detected by computer-assisted-diagnosis. In light of the CAD results, the patient, whose longitudinal MRIs are shown in FIGS. 2D-2F, elected to have a resection; pathological examination revealed a WHO grade 3 oligodendroglioma, a diagnosis that mandated therapeutic intervention. For this patient it was noted that whereas the current surgical option is a subtotal resection (FIG. 2F), a gross total resection was a possible requirement at the time-to-growth detected by computer-assisted-diagnosis (FIG. 2E).

Imaging Abnormality Group: Computer-assisted-diagnosis did not detect growth in any of the 7 patients followed for an imaging abnormality. These patients were followed for an average of 79 months (IQR=68.5 months) after the first MRI.

Review of Predictions of Change-of-Point Method: The visual reviewers reviewed and agreed with the determinations of growth (true positives, n=34+13) and no growth (true negatives, n=9+5) at the times predicted by the statistical online change-of-point method (FIGS. 2A-2H).

Nonlinear Stationary Growth: The data demonstrate that time-to-growth detected with the aid of the computer-assisted-diagnostic method can be several years earlier than visual comparison (Table 3); hence, the importance of the rate of tumor growth. Simulations of the mathematical model of gliomas reveal that growth can be either nonlinear or almost linear as a function of the mitotic rate (FIG. 1G); small mitotic rates generate nonlinear curves. Using the normalized data of the 47 tumors with growth (n=47; 34 of Table 3, and 13 of Table 3), 14/47 tumors were identified whose normalized growth curves fit a nonlinear exponential model (FIG. 1H, R-Square=0.86). It was noted that though 22/29 tumors in the clinical progression group continued to grow after the time-to-growth highlighted by the computer-assisted-diagnostic method (FIG. 1A), 7 low-grade gliomas remained in a stationary phase of slow growth (Table 5), which lasted for longer than 3 years in 3 gliomas (FIG. 1B and FIGS. 2A-2C), 18 months (2 glioma), 14 months (1 glioma) and 9 months (1 glioma).

TABLE 5

Stationaty Growth in the Clinical Progression Group.

| Pathology | Number | 9 months | 14 months | 18 month | ≥3 years |
|---|---|---|---|---|---|
| Oligodendroglioma | 1/29 | | | | 1 |
| Astrocytoma | 5/29 | 1 | 1 | 2 | 1 |
| Mixed gliomas | 1/29 | | | | 1 |
| All | 7/27 | 1 | 1 | 2 | 3 |

Number of patients in the clinical progression group with stationary/slow growth after the time-to-growth detected by computer-assisted-diagnosis lasting for 9 months, 14 months, 18 months, and longer than 3 years.

3D Growth is Nonhomogeneous: Currently, clinical trials compute the size of a glioma as the bi-dimensional product of the two largest perpendicular diameters in the 2D section that includes the largest tumor. This practice assumes that a glioma grows uniformly in 3D; i.e. it grows at equal rates in all directions. However, FIGS. 3A-3J shows a contrasting example, where tumor growth was not homogeneous in 3D because the tumor grew faster at sections away from the largest axial tumor component.

Discussion

Visual comparison of longitudinal radiological studies is widely used in oncology. In all cases, 2D computed tomography or MR images are examined to diagnose 4-dimensional objects, i.e. a change in volume over time. Here, 165 gliomas were screened and the data of a total of 63 patients was analyzed, including 627 MRIs. Unexpectedly, large differences were found between growth detection by visual comparison alone and by visual reviewers aided by the computer assisted method.

Figure 4:
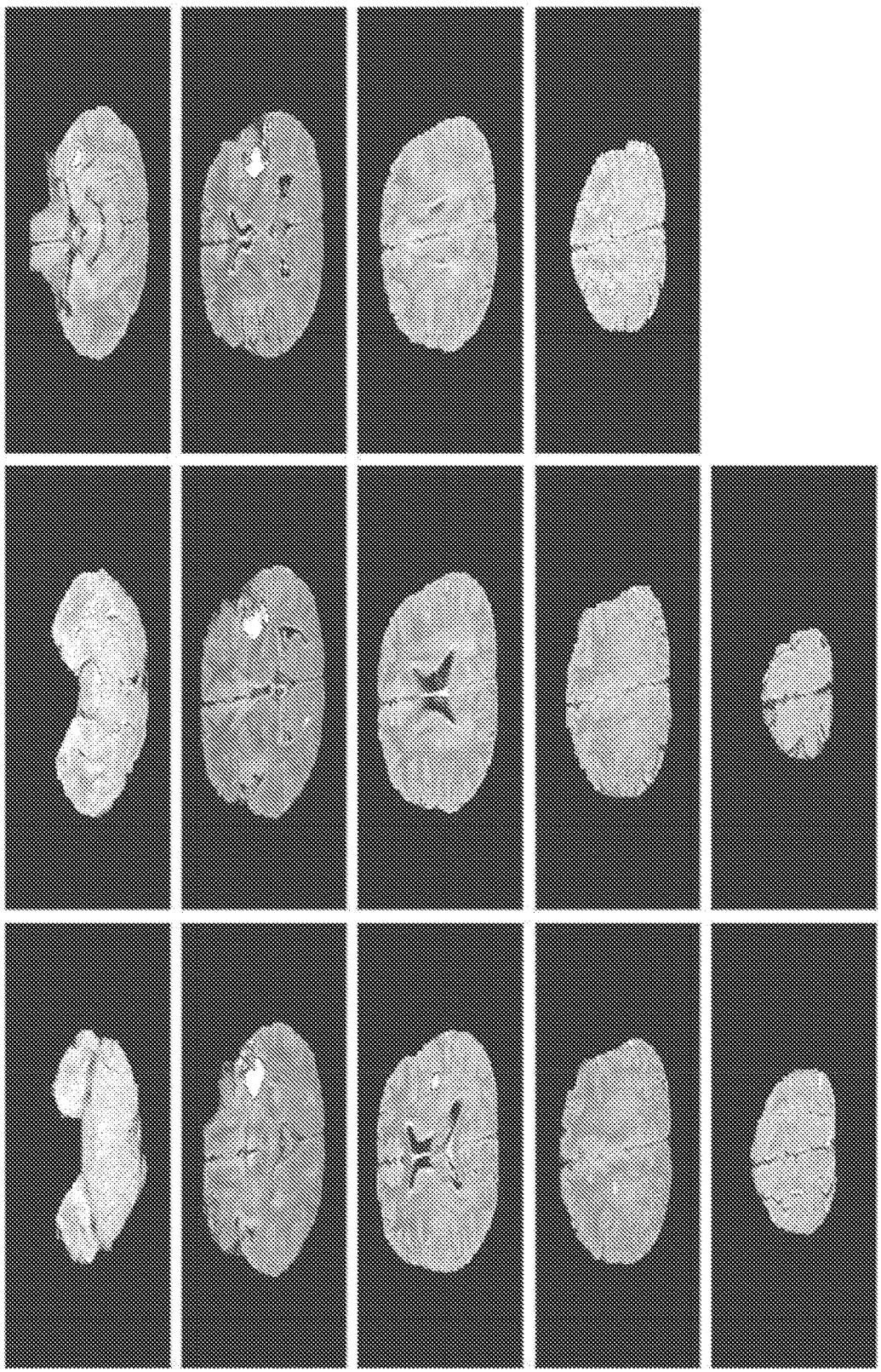
FIG. 4 shows an MRI of tumor 4385 according to the present disclosure at time 0.
Figure 5:
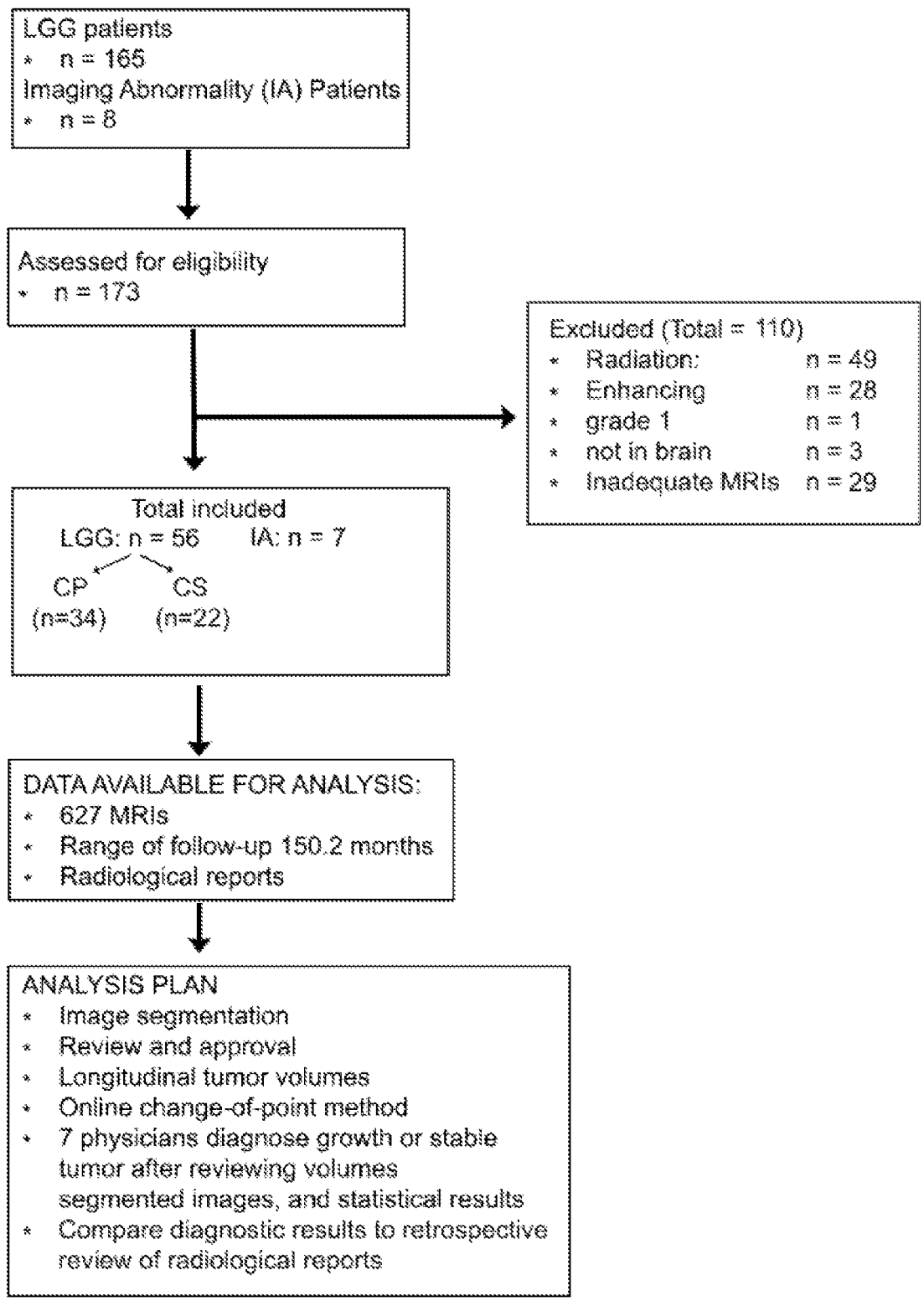
FIG. 5 is an embodiment of a flow diagram and analysis plan according to the present disclosure.

Because low-grade gliomas are followed for several years the current MRIs were compared to all previous studies. Reasons for missing growth by visual inspection can include: 1) the large number of prior studies, which take a long time for image interpretation, 2) the current practice of comparing the current MRI to only a couple of MRIs immediately preceding it, 3) the lack of determination of the baseline MRI, and 4) small changes from one study to the next, but these incremental changes add up over time, 5) comparing single 2-dimensional images misses growth in the third dimension (FIGS. 3A-3J), i.e. in sections away for the largest tumor component (e.g. cases 4384, 4385 (FIG. 4), 6936, 7492, 7505, and 7736 in Example 2), and 6) the baseline volume appears to be a factor for detecting growth by visual comparison; for example, the tumor in FIG. 1C (case 7504), whose baseline volume is 42% of the tumor in FIG. 1B (case 7490), was deemed stable after growing 6 folds whereas the growth of the tumor in FIG. 1B was detected after it grew by only 2-fold.

A retrospective analysis of radiological reports yielded an unaltered view of the landscape of the diagnostic imaging of gliomas at a tertiary Brain Tumor Center. In analyzing longitudinal measurements of tumor volumes, the problem concerns both detecting whether or not a change in tumor volume has occurred and identifying the time of any such change. These questions are addressed by combining tumor segmentation with the change-of-point analysis of the disclosure.

Several segmentation methods including computer vision have recently been developed (Brain lesion (2018) Glioma, Multiple Sclerosis, Stroke and Traumatic Brain Injuries. Heinz, ed. Springer International Publishing). Computerassisted-diagnosis improves the detection of growth in grade 2 gliomas by contouring the tumor margins and generating a signal that directs the attention of the physician towards a change of point (FIGS. 2A-2H). The method of the disclosure is semi-automated, i.e. the final tumor contouring requires additional assessment. This method has been ranked among the top three methods, statistically equivalent with two other methods competing in the BraTS2016 challenge (Bakas et al., (2018) *Progression Assessment, Overall Survival Prediction BRATS Challenge*).

The segmentation method of the disclosure differs from (and is an improvement compared to) deep-learning algorithms as it does not require offline training of a library of reference images. The online change-of-point method is a well-suited statistical method to simulate the clinic visit as it considers only past measurements at each time point. It is preferred over than the fixed threshold method because it handles all types of time-ordered data including data from non-normal distributions and data with outliers (Brodsky (1993) *Nonparametric Methods in Change-Point Problems*: Springer, Netherlands; 1993; Killick & Eckley 2012) *J. Am. Statis. Assoc.* 107: 1590-1598). To exclude changes caused by surgical intervention, the baseline MRI was taken as the one that corresponds to the first minimal volume after resection.

Figure 1E:
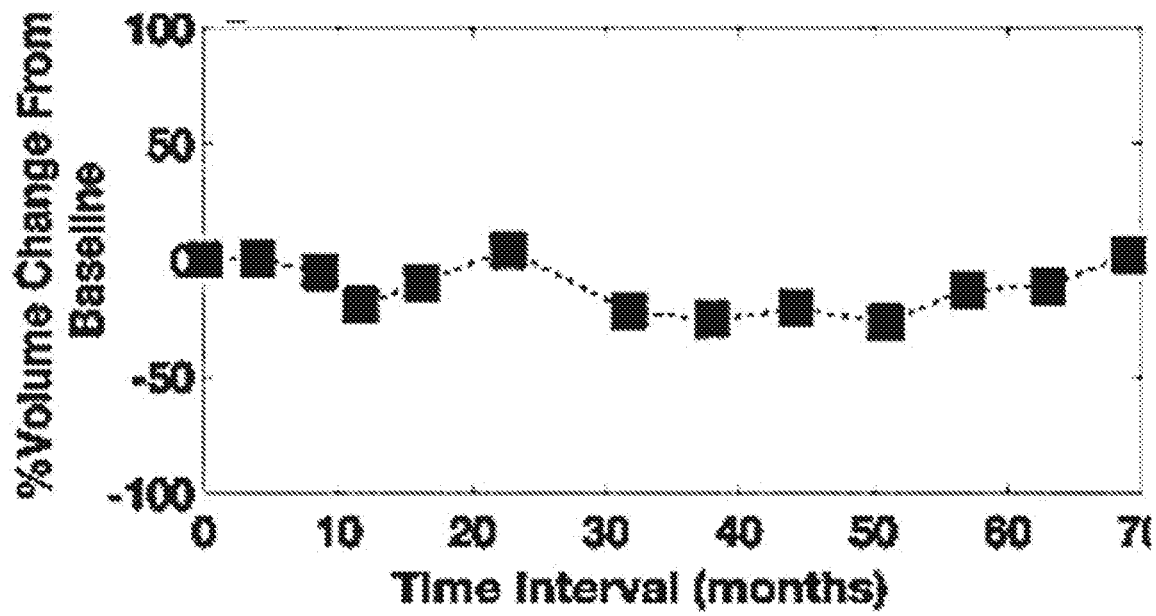
Figure 1G:
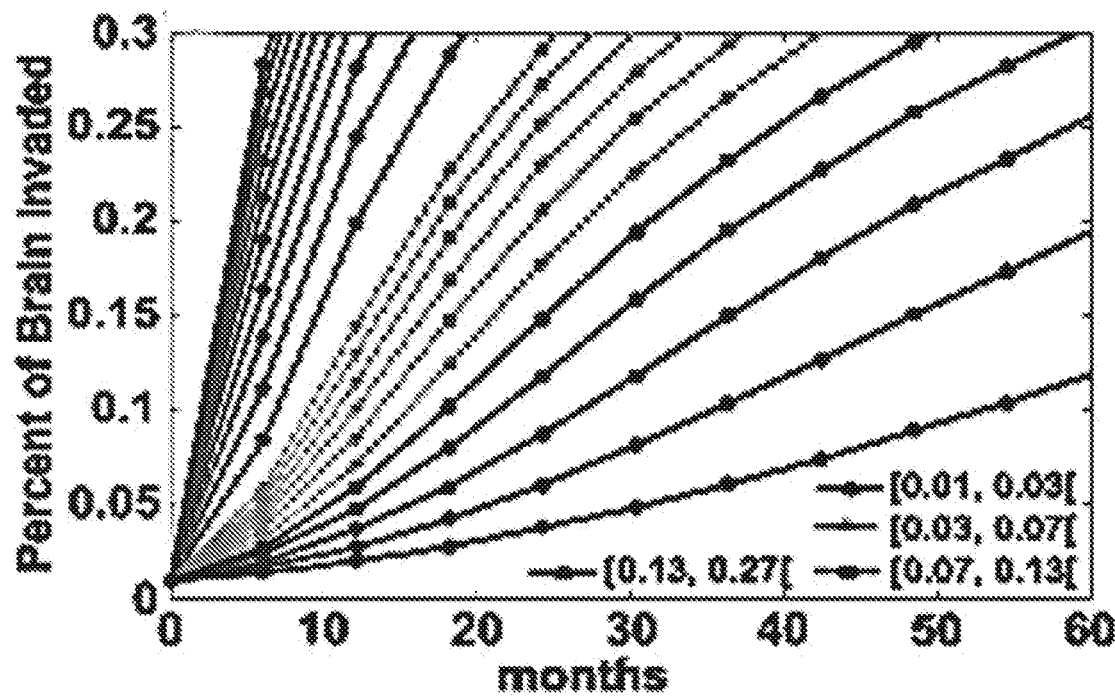
Figure 1F:
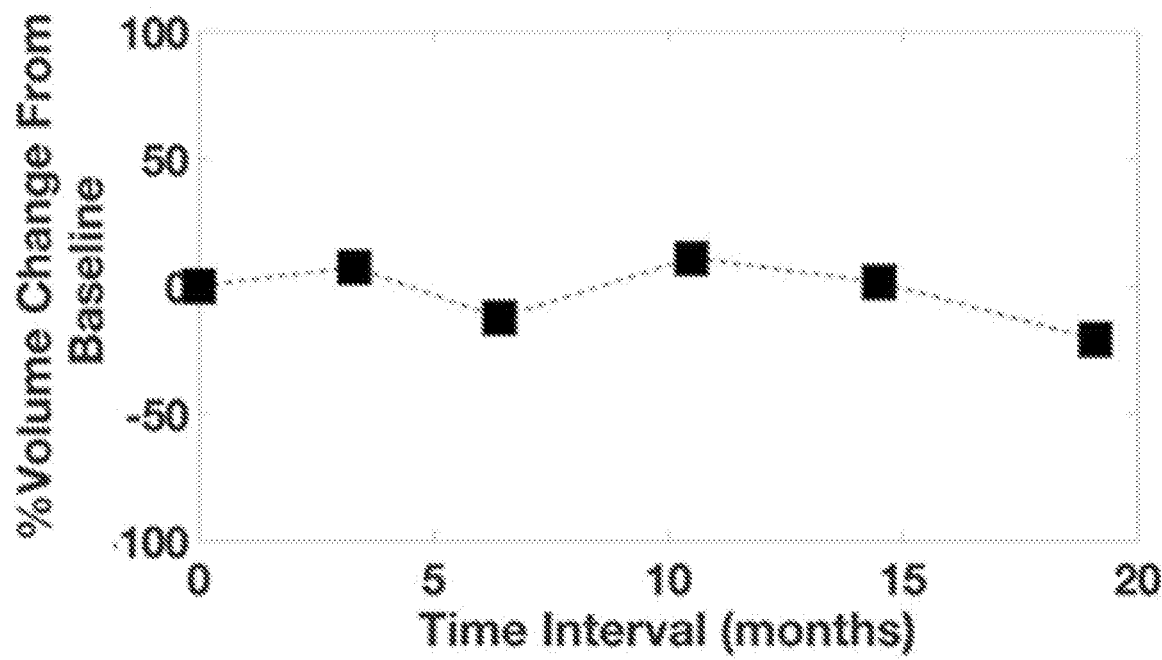
Figure 1H:
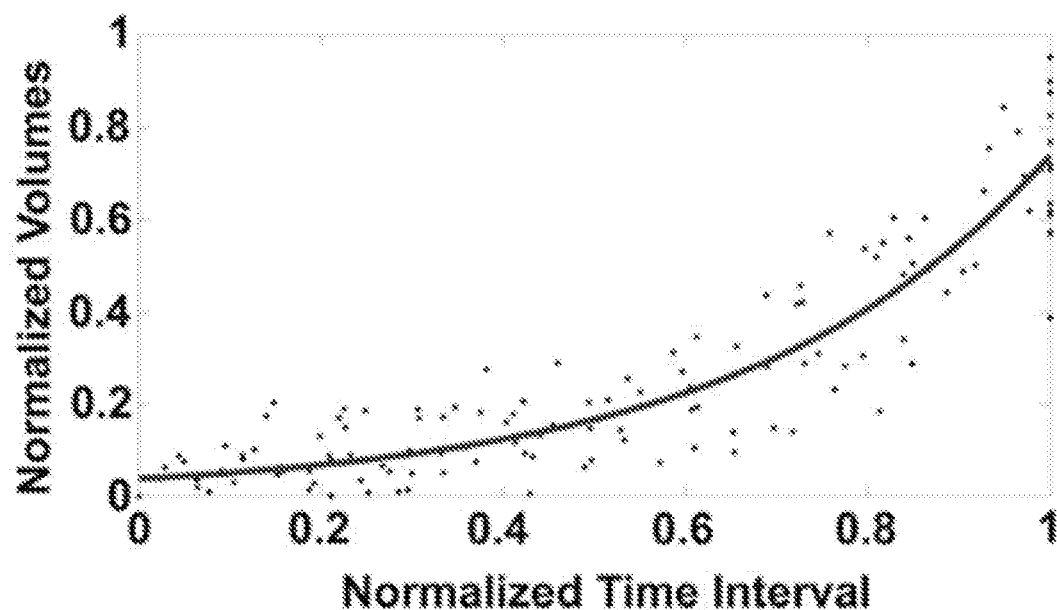

Analysis of the 117 measurements of the 13 true negative curves, i.e. stable by CAD and visual reviews, yields a mean and standard deviation of 0.99% and 26.54%, respectively (FIGS. 1E and 1F). FLAIR images have a variable quality; however lower quality images are more likely to underestimate than over-estimate the truth because CAD uses a physician-in-the-loop approach whereby a visual review must be made and the physician approve both the segmentation results and the determination of growth. Because the reviewer eliminates false positive segmentations and outliers, it is believed that the higher measurement of fluctuating volumes may more closely define the tumor change.

An objective of the CAD of the disclosure is to point the attention towards a potential growth event; the physician has the final responsibility to approve or not. It is argued that minimizing false negatives (even at the cost of potential false positives) is prudent and of the best interest of the patient. For instance, if a case similar to the one shown in FIG. 1A is considered, it is possible that a physician may disapprove of the first growth signal. However, the numerous and continuous alerts starting at month 19 should reduce the likelihood of the tumor being allowed to grow unchecked until month 80. False-positive signals were not encountered in the present datasets as the visual reviews correlated with the change-of-point detection. Nonetheless, false positives are frequent, one can increase the stringency of the change-of-point method by varying the threshold or by considering the second or third change of points.

Tumor assessments in 2D and 3D differ with respect to magnitudes. The methods of the present disclosure evaluates and compares longitudinal volumes of low-grade gliomas. In clinical trials, tumor progression is currently assessed by studying 2D sections of the brain that include the largest component of the tumor; progression is determined when the product of two perpendicular lines increases by 25%. For example, a 12% increase in each of two dimensions generates a 25% increase in the product in 2D ($1.12^2$=1.25). Multiplying by a third dimensional increase of 12% leads to a 41% increase in the volume ($1.12^3$=1.41). Similarly, a 20% and 25% increase in each dimension produce a 73% and 95% increase in volume, respectively. Conversely, a 300% increase in volume can be generated by a 44% increase in each dimension ($1.44^3$=3).

The numerical growth charts suggest that low-grade gliomas may be distinguished not only by their pathological diagnosis but also by their rates of growth (FIGS. 1A-H and FIGS. 3A-3J). For example, the tumor shown in FIG. 1A grew at a faster rate than the tumors shown in FIGS. 1B-1D. The volumetric analysis permits the computation of the rates of growth of low-grade gliomas over time, a biological marker that may enhance tumor classification and guide therapy.

It is evident that the volumetric data of the computer-assisted method is advantageous to physicians detecting growth of LGG significantly earlier than the current practice of visual comparison (Tables 3 and 4). In general, earlier time-to-growth and smaller tumor volumes are desirable because there is evidence that smaller tumors are associated with smaller fields of radiation, optimal surgical resections (see FIGS. 2D-2F), and longer survival times with less neurological morbidity (Claus et al., (2005) *Cancer* 103: 1227-1233; Johannesen et al., (2003) *J. Neurosurg.* 99: 854-862; McGirt et al., (2009) *J. Neurosurg.* 110: 156-162; Nakamura et al., (2000) *Oncology* 58: 108-116; Ahmadi et al., (2009) *Acta Neurochir.* (Wien) 151: 1359-1365; Smith et al., (2008) *J. Clin. Oncol.* 26: 1338-1345; Sanai & Berger (2008) *Neurosurgery* 62: 753-764; Baumert et al., (2016) Lancet Oncol. 17: 1521-1532; Jhaveri et al., (2018) Cancer 124: 1169-1178). Accordingly, early interventions for cases where: 1) the new growth is in the proximity of key nonsurgical structures like the corpus callosum, 2) the rate of growth is elevated, or 3) the tumor is sensitive to chemotherapy can be indicated by application of the methods of the disclosure.

Because low-gliomas grow at variable but slow rates, clinicians need to compare a large number of longitudinal images spanning several months or years leading to significant delays in detection of tumor enlargement. Readily available computer generated tumor outline combined with longitudinal volumetric data and the identification of a statistically significant change-of-point aid a rapid diagnosis of tumor enlargement. Hence, the CAD methods of the disclosure could avoid unpredictable delays and improve the determination of efficacy of new therapeutic interventions. Furthermore, early growth detection offers the potential of lowering morbidity, and perhaps mortality, of patients with low-grade gliomas, which needs to be tested in prospective studies.

What is claimed:

1. A method for determining tumor status in a subject, the method comprising the steps of:
   (a) obtaining a first plurality of sectional images of a low-grade solid tumor in a human or animal subject;
   (b) computing a first volume of the tumor from the first plurality of sectional images;
   (c) obtaining a second plurality of sectional images of the tumor after a period from step (a);
   (d) computing a second volume of the tumor from the second plurality of sectional images;
   (e) determining the extent of tumor increase by comparing the first volume of the tumor from step (b) with the second volume of the tumor volume in step (d) by applying an online abrupt change-of-point method to the plurality of sectional images; and
   (f) modifying a treatment protocol of the human or animal patient to reduce at least one of (i) the rate of increase of the tumor volume and (ii) the volume of the tumor.

2. The method of claim 1, wherein the plurality of sectional images from the subject are generated with an imaging scanner.

3. The method of claim 1, wherein the plurality of sectional images are magnetic resonance images, positron emission tomography images, or computer tomography images.

4. The method of claim 1, wherein in step (a) and (c) the human or animal subject is administered a contrast agent that enhances the plurality of images of the tumor.

5. The method of claim 1, wherein the tumor is a tumor of the brain.

6. The method of claim 5, wherein the tumor is an oligodendroglioma or an astroglioma.

* * * * *